United States Patent
Lazar et al.

(10) Patent No.: US 8,657,757 B2
(45) Date of Patent: Feb. 25, 2014

(54) SYSTEM AND METHODS FOR THE MEASUREMENT OF LUNG VOLUMES

(75) Inventors: Avi Lazar, RaAnana (IL); Ori Adam, Rechovot (IL)

(73) Assignee: Pulmone Advanced Medical Devices, Ltd., Ra'anana (IL)

( * ) Notice: Subject to any disclaimer, the term of this patent is extended or adjusted under 35 U.S.C. 154(b) by 695 days.

(21) Appl. No.: 12/830,955

(22) Filed: Jul. 6, 2010

(65) Prior Publication Data

US 2010/0286548 A1    Nov. 11, 2010

Related U.S. Application Data

(63) Continuation-in-part of application No. 12/670,661, filed as application No. PCT/IL2008/001031 on Jul. 27, 2008.

(60) Provisional application No. 60/951,998, filed on Jul. 26, 2007.

(51) Int. Cl.
*A61B 5/08*    (2006.01)
(52) U.S. Cl.
USPC .......................................... 600/538; 600/529
(58) Field of Classification Search
USPC .................................................. 600/529–543
See application file for complete search history.

(56) References Cited

U.S. PATENT DOCUMENTS

| | | | |
|---|---|---|---|
| 3,100,620 A | 8/1963 | Kates | |
| 4,307,730 A * | 12/1981 | Korn | 600/541 |
| 4,930,498 A | 6/1990 | Hayek | |
| 5,233,998 A | 8/1993 | Chowienczyk et al. | |
| 5,261,397 A * | 11/1993 | Grunstein | 128/204.18 |
| 5,857,459 A | 1/1999 | Snow et al. | |
| 6,066,101 A | 5/2000 | Johnson et al. | |
| 6,183,423 B1 | 2/2001 | Gaumond et al. | |
| 6,723,055 B2 | 4/2004 | Hoffman | |
| 2004/0186390 A1 | 9/2004 | Ross et al. | |
| 2004/0249300 A1 | 12/2004 | Miller | |
| 2006/0264772 A1 * | 11/2006 | Aljuri et al. | 600/538 |
| 2006/0276807 A1 | 12/2006 | Keast et al. | |

(Continued)

FOREIGN PATENT DOCUMENTS

WO    WO 2009/013755    1/2009

OTHER PUBLICATIONS

Supplemental European Search Report; Application No. 08789707.0 dated Jan. 31, 2013, 7 pages.

(Continued)

*Primary Examiner* — Patricia Mallari
*Assistant Examiner* — Tiffany Weston
(74) *Attorney, Agent, or Firm* — Fish & Richardson P.C.

(57) ABSTRACT

A method for determining a pulmonary volume change includes: receiving a respiration event from a subject in an airflow chamber; interrupting the respiration event by an occlusion of the airflow chamber initiated at a first time instant and terminated at a second time instant subsequent to the first time instant; taking a plurality of measurements of airflow rate through the airflow chamber between the second time instant and a third time instant subsequent to the second time instant; and determining a pulmonary volume change substantially equal to a reduction of a pulmonary air volume by a pulmonary response air volume and a normal air volume, wherein the pulmonary volume change is related to a change in density of air in the airflow chamber.

24 Claims, 24 Drawing Sheets

(56) References Cited

U.S. PATENT DOCUMENTS

| | | |
|---|---|---|
| 2007/0135724 A1 | 6/2007 | Ujhazy et al. |
| 2007/0142742 A1 | 6/2007 | Aljuri et al. |
| 2007/0185406 A1 | 8/2007 | Goldman |
| 2008/0077033 A1 | 3/2008 | Figueiredo et al. |

OTHER PUBLICATIONS

International Preliminary Report and Written Opinion; Application No. PCT/IL2011/000533, issued Jan. 8, 2013, 7 pages.
International Preliminary Report and Written Opinion; Application No. PCT/IL2008/001031, issued Jan. 26, 2010, 7 pages.
Notification of Transmittal of the International Search Report and the Written Opinion of the International Searching Authority, or Declaration (1 page); International Search Report (3 pages); and Written Opinion of the International Searching Authority (6 pages), mailed Dec. 14, 2011, for related international application PCT/IL11/00533.
Authorized officer, Simin Baharlou, International Preliminary Report on Patentability, International Application No. PCT/IL11/00533, mailed Jan. 17, 2013, 8 pages.

* cited by examiner

SYSTEM AND METHODS FOR THE MEASUREMENT OF LUNG VOLUMES

CLAIM OF PRIORITY

This application is a continuation-in-part application of U.S. patent application Ser. No. 12/670,661, filed Jan. 26, 2010, which is a National Phase of PCT Patent Application No. PCT/IL2008/001031 having an International filing date of Jul. 27, 2008, which claims the benefit of U.S. Provisional Patent Application No. 60/951,998, filed on Jul. 26, 2007. The contents of the above applications are all incorporated herein by reference.

TECHNICAL BACKGROUND

The present disclosure relates to methods and a device for measuring pulmonary function parameters and, more particularly, to a method and a device for calculating pulmonary function parameters according to pulmonary volumetric indicators.

BACKGROUND

Absolute lung volume is a key parameter in pulmonary physiology and diagnosis but is not easy to measure in the live individual. It is relatively straightforward to measure the volume of air which is exhaled from a subject's mouth but at the end of complete exhalation, a significant amount of air is always left in the lungs because the mechanical properties of the lungs and chest wall, including the ribs, do not allow the lungs to collapse completely. The gas left in the lungs at the end of a complete exhalation is termed the Residual Volume (RV) which may be significantly increased in disease. The total volume of gas in the lungs at the end of a maximal inspiration is termed the Total Lung Capacity (TLC) which includes the RV plus the maximum amount of gas which can be inhaled or exhaled and which is termed the Vital Capacity (VC). However, during normal breathing the subject does not empty the lungs down to RV nor inflate them to TLC. The amount of gas in the lungs at the end of a normal breath, as distinct from a complete exhalation, is termed the Functional Residual Capacity (FRC) or Thoracic Gas Volume (TGV), depending upon the manner in which it is measured. For simplicity when this volume is measured by inert gas dilution techniques it will be termed FRC and when measured by barometric techniques involving gas compression as in this application it will be termed TGV.

In order to determine the total volumes of gas in the lungs at TLC, TGV or RV, indirect methods must be used since it is impossible to completely exhale all the gas from the lungs. There are two basic techniques currently available, gas dilution and whole body plethysmography (a barometric method). Gas dilution involves the dilution of a known concentration and volume of inert gas by the gas in the lungs of the subjects and is critically dependent on complete mixing of the marker gas and lung gas. In subjects with poor gas mixing due to disease, this technique is very inaccurate and generally underestimates the true FRC. In the whole body plethysmograph, the subject makes respiratory efforts against an obstruction within a gas tight chamber and the changes in pressure on the lung side of the obstruction can be related to the changes in pressure in the chamber through Boyle's law to calculate TGV. This method accurately measures TGV even in sick subjects but requires complicated and expensive equipment and is difficult to perform.

Once FRC (gas dilution), or TGV (whole body plethysmograph), is calculated, the measurement by spirometry of the extra volume of gas which can be exhaled from the end of a normal exhalation (Expiratory Reserve Volume, ERV) and the extra volume which can be inhaled from the end of a normal exhalation (Inspiratory Capacity, IC) allows the calculation of TLC and RV.

These three important indicators (TLC, RV and FRC or TGV) are mutually connected through the following formulas: RV=FRC−ERV and TLC=FRC+IC and, TLC=RV+ERV+IC=RV+VC.

If FRC is determined by gas dilution and TGV by a barometric method, then the difference between them (TGV minus FRC) is a measure, albeit approximate, of the volume of poorly ventilated or "trapped gas" in the lungs.

In healthy subjects TGV and FRC should be virtually identical as there is little or no trapped gas, hence, for all practical matters, the term TGV shall apply for FRC as well. In summary, determination of TLC, TGV and RV is central to the complete evaluation of lung function.

The driving force for the respiratory airflow in the airways is the pressure gradient between the alveoli and the atmosphere, which is produced by virtue of the pressure change in the lungs arising from the rhythmic respiratory motion of the chest. The rate of this flow is directly proportional to the pressure gradient and the cross section of the respiratory airways, while being inversely proportional to the total airway length and to the viscosity of the gas. Pulmonary airway resistance is primarily dependent on the length and cross section of the respiratory airways and on the properties of the surface interface with the moving air.

It is particularly diagnostically helpful to measure the alveolar pressure under certain conditions, such as when there is additional resistance to respiration, during gravitational overloading, respiration under elevated or reduced pressures, inspiration of gas mixtures differing in density and composition from atmospheric air, and so on.

One of the most common methods for measuring alveolar pressure is the airway interruption method, see Sawashima, M., Honda, K., Niimi, S. & Hirose, H. [1986], some clinical data on aerodynamic examination using the airway interruption method. Ann. Bull. RILP, 20, 217-224, which is incorporated herein by reference. This method is commonly utilized for estimating the resistance of the lower respiratory tract in pulmonary diseases. In this method, respiratory airflow is momentarily interrupted by a shutter attached to the mouth of the user via a mask covering the face of the user or some other method. Upon the occlusion of airflow at the mouth by the shutter, the air pressure measured at the shutter is indicative of the alveolar pressure once equilibrium between the pressure at the mouth and the alveolar pressure is obtained.

The calculation of airway resistance and other parameters involving alveolar pressure relies on the assumption that pressure at the mouth or airways approximates alveolar pressure. However, the instant following the interruption at which mouth and alveolar pressure are at full equilibrium cannot always be ascertained using the interrupter method. Mouth and alveolar pressure equilibration is not instantaneous, but rather may require over 100 milliseconds (ms) to be achieved, which in many application exceeds the duration of the interruption by the interruption device. See Ohya N., Huang J., Fukunaga T., Toga H. Mouth Pressure curve on abrupt interruption of airflow during forced expiration. J. Appl. Physiol. 1989; 66: 509-517 and Ohya N., Huang J., Fukunaga T., Toga H. Mouth Pressure curve on abrupt interruption of airflow during forced expiration. J. Appl. Physiol. 1989; 66: 509-517 which are incorporated herein by reference, In some patients, the prolonged equilibration of mouth and alveolar pressure may occur even during quiet breathing, see Hage R., Aerts J. G. J. V., Verbraak A. F. M., van den Berg B., Bogaard J. M. Detection of flow limitation during tidal breathing by the interrupter technique. Eur Respir J, 1995, 8, 1910-1914.

In some instances, measuring airway resistance may occur by approximating the alveolar pressure by linear back extrapolation of the averaged pressure reading at $t_0+70$ ms and $t_0+30$ ms to $t_0+15$ ms where $t_0$ is the instant of full occlusion. If, for example in some patients, full mouth and alveolar pressure equilibration is achieved after periods longer than 15 ms, the approximated alveolar pressure will be erroneously approximated. Furthermore, the pressure slope during mouth and alveolar pressure equilibration and the slope following full equilibration are different because they reflect different physical processes. Thus, an extrapolation method which includes the contributions of the pressure slope prior to and post equilibration will result in an erroneous approximation of alveolar pressure.

The estimation of pulmonary properties dependent on alveolar pressure, such as airway resistance (which is proportional to alveolar pressure), using the interrupter method in patients suffering from airway obstruction or flow limitation may therefore be erroneous due to extended mouth and alveolar pressure equilibration, and may lead to misdiagnosis of the type and severity of the pulmonary disorder in these patients.

SUMMARY OF THE INVENTION

In one general embodiment, a method for determining a pulmonary volume change includes the steps of: receiving a respiration event from a subject in an airflow chamber; interrupting the respiration event by an occlusion of the airflow chamber initiated at a first time instant and terminated at a second time instant subsequent to the first time instant; taking a plurality of measurements of airflow rate through the airflow chamber between the second time instant and a third time instant subsequent to the second time instant; and determining a pulmonary volume change substantially equal to a reduction of a pulmonary air volume by a pulmonary response air volume and a normal air volume, wherein the pulmonary volume change is related to a change in density of air in the airflow chamber.

In another general embodiment, a method for enhancing a deviation of alveolar pressure from a base pressure includes the steps of receiving a respiration event from a subject in an airflow chamber; interrupting the respiration event by an occlusion of the airflow chamber initiated at a first time instant and terminated at a second time instant subsequent to the first time instant; subsequent to an instant when alveolar and mouth pressure are substantially equal, performing a volume-change event between a third time instant and a fourth time instant, wherein the third and fourth time instants are between the first time instant and the second time instant, and the volume-change event includes an adjustment of air volume in a closed air chamber comprising the airflow chamber and at least a portion of a pulmonary system of the subject; and measuring a pressure in the airflow chamber during the volume-change event.

In another general embodiment, a breathing apparatus for monitoring pulmonary attributes of a subject includes: an airflow chamber; a shutter in fluid communication with the airflow chamber, where the shutter is adapted to rapidly adjust from an open state to a closed state to occlude airflow through the chamber to initiate an occlusion event and rapidly adjust from the closed state to the open state to facilitate airflow through the chamber to terminate the occlusion event, and where at least one of the airflow chamber and the shutter are adjustable to vary a resistance to airflow through the chamber; a flow sensor adapted to measure airflow through the airflow chamber; a pressure sensor adapted to measure pressure in the airflow chamber; a micro-processor based controller communicably coupled to the flow sensor and the pressure sensor; and an interface communicably coupled to the controller and including a graphical user interface (GUI), where the GUI is adapted to display a plurality of panels comprising pulmonary attributes of the subject.

In another general embodiment, a method for determining an alveolar pressure of a subject includes: receiving a respiration event from the subject in an airflow chamber; taking a first plurality of measurements of pressure in the airflow chamber during the respiration event; interrupting the respiration event by an occlusion of the airflow chamber initiated at a first time instant and terminated at a second time instant subsequent to the first time instant; taking a second plurality of measurements of pressure in the airflow chamber between the first time instant and a third time instant, where the third time instant is subsequent to the second time instant; and determining the pressure in the airflow chamber at a fourth time instant between the first and second time instants, where an alveolar pressure of the subject is substantially equal to the pressure in the airflow chamber at the fourth time instant.

In one aspect of one or more general embodiments, determining a pulmonary volume change substantially equal to a reduction of a pulmonary air volume by a pulmonary response air volume and a normal air volume may include: determining a pulmonary air volume based on the plurality of measured airflow rates; determining a normal air volume; and determining a pulmonary response air volume between a fourth time instant and a fifth time instant.

In one aspect of one or more general embodiments, determining a normal air volume may include: determining a normal airflow rate of the respiration event between the second time instant and the third time instant, where the normal airflow rate is substantially equal to an airflow rate that would have existed between second and third time instants in the absence of the interruption by the occlusion of the airflow chamber; and integrating the normal airflow rate between the second and third time instants.

In one aspect of one or more general embodiments, determining a normal airflow rate of the respiration event between the second time instant and the third time instant may include: measuring a normal airflow rate for a time period prior to the first time instant; measuring the normal airflow rate for a time period subsequent to the third time instant; and determining the normal airflow rate between the second and third time instants by interpolating from the measured normal airflow rates prior to the first time instant and subsequent to the third time instant.

In one aspect of one or more general embodiments, the interpolation may be one of: a spline interpolation; an exponential interpolation; and a polynomial interpolation.

In one aspect of one or more general embodiments, determining a normal airflow rate of the respiration event between the second time instant and the third time instant may include: measuring at least one of a normal airflow rate for a time period prior to the first time instant and the normal airflow rate for a time period subsequent to the third time instant; and determining the normal airflow rate between the second and third time instants by extrapolation from one of the measured normal airflow rate prior to the first time instant and the measured normal airflow rate subsequent to the third time instant.

In one aspect of one or more general embodiments, determining a normal airflow rate of the respiration event between the second time instant and the third time instant may include: measuring at least one of a normal airflow rate for a time period prior to the first time instant, measuring pressure between the first time instant and the second time instant; and determining the normal airflow rate between the first time instant and the second and third time instants by relating changes in pressure with changes in normal airflow rate.

In one aspect of one or more general embodiments, determining a pulmonary response air volume between a fourth time instant and a fifth time instant may include: determining a fourth time instant when the measured airflow rate is initially substantially equal to the normal airflow rate subsequent to the second time instant; determining a fifth time instant when a trend change in the measured airflow rate occurs, subsequent to the second and fourth time instants; determining a pulmonary response airflow rate between the fourth and fifth time instants; and integrating the pulmonary response airflow rate between the fourth and fifth time instants inclusively.

In one aspect of one or more general embodiments, a method may further include integrating the pulmonary response airflow rate between the fifth and third time instants inclusively; and reducing the integral of the normal flow rate between the second and third time instants.

In one aspect of one or more general embodiments, interrupting the respiration event by an occlusion of the airflow chamber may include applying an external pressure on a combination of a portion of the subject's pulmonary system and the airflow chamber.

In one aspect of one or more general embodiments, taking a plurality measurements of airflow rate through the airflow chamber may include measuring a pressure change in the airflow chamber of the respiration event at a plurality of instants between the second time instant and the third time instant.

In one aspect of one or more general embodiments, a method may further include converting the measured pressure changes to a plurality of airflow rates related to the measured pressure changes and one or more dimensions of the airflow chamber.

In one aspect of one or more general embodiments, the method may further include determining an instantaneous volume of air in the lungs of the subject based on the pulmonary volume change.

In one aspect of one or more general embodiments, determining an instantaneous volume of air in the lungs of the subject based on the pulmonary volume change may include: determining a change in pressure in the lungs of the subject; determining a base pressure substantially equal to atmospheric pressure; and calculating the instantaneous volume of air in the lungs of the subject based on the pulmonary volume change, the change in pressure in the lungs, and the base pressure.

In one aspect of one or more general embodiments, the instantaneous volume of air in the lungs of the subject may be substantially equal to an instantaneous volume of air in the lungs of the subject at the first time instant.

In one aspect of one or more general embodiments, determining a change in pressure in the lungs of the subject may include: measuring a pressure in the airflow chamber at the first time instant; measuring a pressure in the airflow chamber at the second time instant; and calculating a difference between the measured pressures at the first and second time instants, where the change in pressure in the lungs of the subject is substantially equal to the calculated difference.

In one aspect of one or more general embodiments, a method may further include determining a residual volume of air in the lungs of the subject based on the determined instantaneous volume of air in the lungs of the subject.

In one aspect of one or more general embodiments, determining a residual volume of air in the lungs of the subject based on the determined instantaneous volume of air in the lungs of the subject may include determining a difference between the determined instantaneous volume of air in the lungs of the subject and a maximum volume of air expirable by the subject during the respiration event, where the residual volume of air in the lungs of the subject is substantially equal to the determined difference.

In one aspect of one or more general embodiments, a method may further include determining a total lung capacity of the subject based on the determined residual volume of air in the lungs of the subject.

In one aspect of one or more general embodiments, determining a total lung capacity of the subject based on the determined residual volume of air in the lungs of the subject may include: determining a sum of the determined residual volume and a vital capacity of the subject, where the vital capacity substantially is equal to a maximum amount of air inhalable or exhalable from the subject, the total lung capacity substantially equal to the determined sum.

In one aspect of one or more general embodiments, a method may further include determining a thoracic gas volume of the subject based on the determined residual volume of air in the lungs of the subject.

In one aspect of one or more general embodiments, determining a thoracic gas volume of the subject based on the determined residual volume of air in the lungs of the subject may include: determining a sum of the determined residual volume and an expiratory reserve volume, where the expiratory reserve volume is substantially equal to a volume of air exhalable from the subject after a normal exhalation of air from the lungs of the subject, and the thoracic gas volume is substantially equal to the determined sum.

In one aspect of one or more general embodiments, the expiratory reserve volume may be determined through a spirometrical measurement.

In one aspect of one or more general embodiments, at least a portion of the airflow chamber may be kept at isothermal conditions.

In one aspect of one or more general embodiments, performing a volume-change event between a third time instant and a fourth time instant may include operating a pump in fluid communication with the airflow chamber to increase the volume of the closed air chamber.

In one aspect of one or more general embodiments, performing a volume-change event between a third time instant and a fourth time instant may include operating a pump in fluid communication with the airflow chamber to decrease the volume of the closed air chamber.

In one aspect of one or more general embodiments, performing a volume-change event between a third time instant and a fourth time instant may include stroking a piston within a cylinder in fluid communication with the airflow chamber to increase the volume of the closed air chamber.

In one aspect of one or more general embodiments, performing a volume-change event between a third time instant and a fourth time instant may include stroking a piston in a cylinder in fluid communication with the airflow chamber to decrease the volume of the closed air chamber.

In one aspect of one or more general embodiments, a method may further include determining a difference in the measured pressure in the airflow chamber during the volume-change event and the pressure in the airflow chamber during equalization.

In one aspect of one or more general embodiments, a method may further include determining a lung compliance of the subject at the first time instant, where the lung compliance is based on the determined difference in the measured pressure in the airflow chamber during the volume-change event and the pressure in the airflow chamber during equalization, an instantaneous lung volume of the subject, and the volume adjustment of the closed air chamber.

In one aspect of one or more general embodiments, determining a lung compliance of the subject at the first time instant may include solving the equation:

$$C_0 = \frac{dV}{P_{d1} - P_{d0}} - \frac{V_0}{P_A},$$

where $C_0$ is the lung compliance of the subject, $dV$ is the volume adjustment of the closed air chamber, $V_0$ is the instantaneous lung volume of the subject, $P_{d1}-P_{d0}$ is the determined difference in the measured pressure in the airflow chamber during the volume-change event, and $P_A$ is an ambient pressure at the first time instant.

In one aspect of one or more general embodiments, determining the pressure in the airflow chamber at a fourth time instant between the first and second time instants may include: determining a second derivative of a curve comprising the first and second plurality of measured pressures; and correlating a fourth time instant between the first and second time instants with an extrema on the second derivative of the curve.

In one aspect of one or more general embodiments, determining the pressure in the airflow chamber at the fourth time instant may include at least one of: interpolating the pressure at the fourth time instant based on the curve comprising the first and second plurality of measured pressures; and extrapolating the pressure at the fourth time instant based on the curve comprising the first and second plurality of measured pressures.

In one aspect of one or more general embodiments, the interpolation may be based on at least one of: a spline interpolation; an exponential interpolation; and a polynomial interpolation.

In one aspect of one or more general embodiments, a method may further include correlating at least one of the first, second, and third time instants with extremas on the second derivative of the curve.

In one aspect of one or more general embodiments, a method may further include determining a pressure slope curve of measured pressure values between the fourth and third time instants; and back extrapolating the pressure curve to a time instant just prior to the fourth time instant to determine a pressure value at the time instant; and estimating the alveolar pressure of the subject from the pressure value at the time instant.

In one aspect of one or more general embodiments, back extrapolating the pressure curve to a time instant just prior to the fourth time instant to determine a pressure value at the time instant occurs subsequent to correlating the fourth time instant between the first and second time instants with the extrema on the second derivative of the curve.

In one aspect of one or more general embodiments, a method may further include determining a change of trend in the pressure slope; and correlating the fourth time instant to a time instant occurring at the change of trend in the pressure slope.

In one aspect of one or more general embodiments, a method may further include determining an amount of work performed by an occluding device between the first and second time instants; and reducing the pressure in the airflow chamber at the fourth time instant according to the determined amount of work.

In one aspect of one or more general embodiments, determining an amount of work comprises integrating an incremental amount of work according to the equation:

$$dW = \int_{t_0}^{t_0+\Delta_{Occlusion}} P\hat{f}\,dt,$$

where $dW$ is the incremental amount of work, $t_0$ is the first time instant, $t_0+\Delta_{Occlusion}$ is the second time instant, $P$ is the pressure measured in the airflow chamber between the first and second time instants, and $\hat{f}$ is a change of rate of airflow through the airflow chamber due to one of the occlusion initiation or the occlusion termination.

In one aspect of one or more general embodiments, an apparatus may further include a user input device communicably coupled to the GUI.

In one aspect of one or more general embodiments, the plurality of panels may include a first panel adapted to display at least one of a total lung capacity, a residual capacity, and a thoracic gas volume over a predetermined time duration.

In one aspect of one or more general embodiments, the plurality of panels may include a second panel adapted to display one or more pressure values measured by the pressure sensor and one or more airflow values measured by the flow sensor during the occlusion event.

In one aspect of one or more general embodiments, the plurality of panels may include a third panel adapted to display one or more pressure values measured by the pressure sensor and one or more airflow values measured by the flow sensor during all or part of a respiration event.

In one aspect of one or more general embodiments, the part of the respiration event may include a respiratory half cycle, and the third panel may be further adapted to display a time duration of the occlusion event during the respiratory half-cycle.

In one aspect of one or more general embodiments, the plurality of panels may include a fourth panel adapted to display an alveolar pressure of the subject during the occlusion event, where the alveolar pressure is calculated by the controller based on one or more pressure values measured by the pressure sensor and one or more airflow values measured by the flow sensor.

In one aspect of one or more general embodiments, the controller may be adapted to receive a command from the user through the user input and adjust the calculated alveolar pressure of the subject in response to the command.

In one aspect of one or more general embodiments, the controller may be adapted to receive a command from the user through the interface to adjust a time instant subsequent to the occlusion event, where the time instant occurs when a measured flow value in the airflow chamber is substantially equal to a measured flow value in the airflow chamber prior to the occlusion event.

In one aspect of one or more general embodiments, the controller may be adapted to receive a command from the user through the interface to set a time duration of the occlusion event.

In one aspect of one or more general embodiments, the time duration may be between approximately 100 ms and 2 seconds.

In one aspect of one or more general embodiments, the controller may be adapted to receive a command from the user through the interface to set a time duration of the occlusion event based on a value of a pressure slope of one or more measured pressure values by the pressure sensor.

In one aspect of one or more general embodiments, the controller may be adapted to receive a command from the user through the interface to adjust a closure setting of the shutter to vary the resistance to airflow through the chamber.

In one aspect of one or more general embodiments, the controller may automatically adjust a closure setting of the shutter to vary the resistance to airflow through the chamber, where the adjustment includes at least one of increasing the resistance to airflow through the chamber during a time duration prior to initiation of the occlusion event and decreasing the resistance to airflow through the chamber during a time duration subsequent to termination of the occlusion event.

In one aspect of one or more general embodiments, the controller may be adapted to calculate a respiratory system compliance index of the subject during an increased resistance to airflow through the chamber by at least one of the shutter and the airflow chamber.

In one aspect of one or more general embodiments, the controller may be adapted to calculate the lung compliance according to the equation:

$$C = \frac{V_a - V_b}{P_{Al}},$$

where C is the lung compliance, $V_a$ is a volume of the lungs of the subject at a time instant of measurement of a pressure in the chamber by the pressure sensor, $V_b$ is a volume of the lungs of the subject when at the end of a normal breath of the subject, and $P_{AL}$ is the alveolar pressure of the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1:
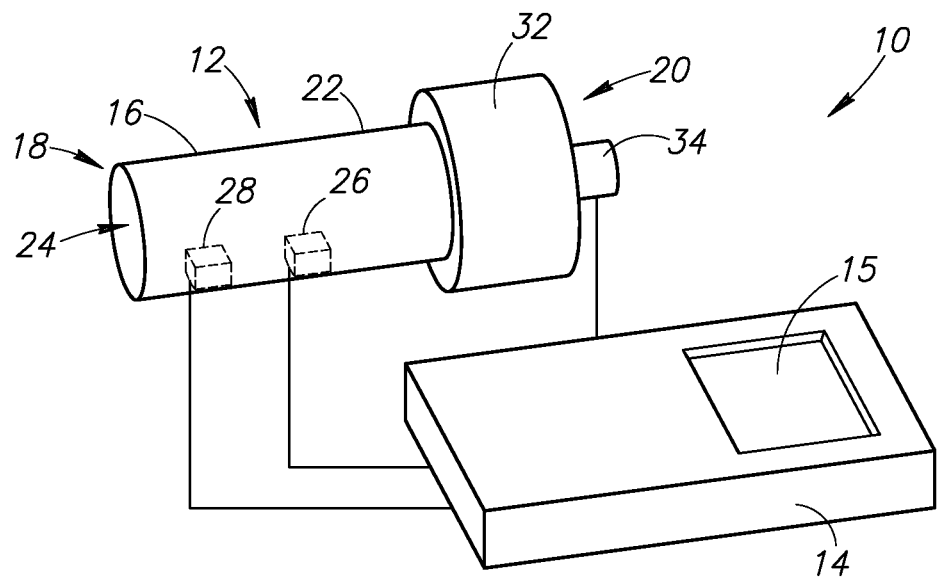
FIG. 1 is a schematic illustration of a system for measurement of respiration parameters, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to a system and methods for determination of lung parameters, and more particularly, determination of Functional Residual Capacity (FRC) Thoracic Gas Volume (TGV), Total Lung Capacity (TLC) and Residual Volume (RV). The system and methods of the present application are designed to directly measure volume in the lungs with a handheld device, without the use of external chambers or belts. The principles and operation of a system and methods according to the present invention may be better understood with reference to the drawings and accompanying descriptions.

For example, according to some embodiments of the present disclosure, there is provided a device and method for estimating an alveolar pressure by interrupting a respiratory airflow of user breathing through a breathing apparatus. The method is based on a recording of an airway pressure in a breathing apparatus during an entire test, and in particular, during an interruption. The recording allows identifying a plurality of instants during the interruption, such as an interruption initiation instant, an interruption termination instant and an instant of full airway and alveolar pressure equilibration. The airway pressure during these instants allows estimating, optionally by interpolation or extrapolation, the airway pressure during other intermediate instants that occur during the interruption, such as estimated alveolar pressure at the instant of interruption. The estimated airway pressure may be negligibly affected by compression or mechanical waves that are caused by the interruption device and therefore provides an accurate estimation on the user's alveolar pressure that would have existed in the absence of an interruption. In addition, the complete occlusion of airways is optionally accomplished within a sufficiently short interval, allowing for an accurate determination of the alveolar pressure at the instant just prior to the interruption.

The method allows determining an airway pressure during an airway and alveolar equilibrium instant by an estimation of said recorded airway pressure according to said recorded airway pressure at each said instant. Optionally, the interrupting is performed by occluding the airway of the user within less than 25 milliseconds, for example, 20, 15 milliseconds, and preferably within less than 10 milliseconds. Further, in some aspects, the user's alveolar pressure is used for correlating pulmonary characteristics during one or more respiration cycles, such as TLC, RV, TGV, tidal volume (TV), lung compliance, airway resistance (AR), and/or any combination thereof.

Additionally, according to some embodiments of the present disclosure, there is provided a method for measuring density related pulmonary volume changes. Optionally, the density related pulmonary volume changes by this method may be used in correlation with the alveolar pressure changes in order to calculate the instantaneous pulmonary volume. The method may be based on a flow rate of a respiratory airflow of a user after a respiratory modulation, such as airway interruption. The flow rate allows determining a volumetric flow subsequent to the respiratory modulation, for example by calculating the integral of the flow rate. A normal respiratory flow that is contributed by a normal respiratory motion and a responsive flow contributed by the respiratory modulation are reduced from the volumetric flow. In such a manner, the reduced volumetric flow reflects the density related pulmonary volume change without the effect of the respiratory modulation and the normal respiratory motion. The reduced volumetric flow may then be outputted, either for presentation to the user or to a physician and/or for correlating pulmonary characteristics, such as TLC, RV, TGV, TV, lung compliance, airway resistance, and/or any combination thereof.

In some aspects, the flow rate is provided by performing the interruption which is outlined before while the user is breathing through a breathing apparatus and recording the flow rate in the breathing apparatus after the interruption. Further, volumetric flow may be determined by calculating an integral of the airflow rate between the termination of the respiratory modulation and a normal flow instant which is subsequent to the respiratory modulation. The termination may be determined according to airway pressure that is measured during the respiratory modulation and the normal flow instant may be detected according to reference values which are recorded before and/or after the respiratory modulation.

In some embodiments of the present disclosure, there is provided a device intended to alter the modulation, while airways are occluded. Optionally, the modulation alteration is in the form of a controlled volume change of a device that is in mass communication with the airways of the subject. Further, an alteration of the modulation may be performed while airways are occluded. The airway pressure changes resulting from the alteration, in correlation with the calculated lung volume at the instant of the alteration are then used to derive an index of respiratory system compliance. According to some aspects, there is provided a number of processes for correlating pulmonary alveolar and/or density related pulmonary volume changes to pulmonary characteristics, such as TLC, RV, TGV, TV, lung compliance, airway resistance, and/or any combination thereof.

As used herein a "user" or "subject" means a healthy user, a subject, or a patient to whom the one or more instantaneous pulmonary measurements relating to the lungs, medical condition and/or respiration, are related. The user may be a person or an animal operating a breathing device, for example as described below, a healthy user. As used herein, an airway means an active airway that allows actively passing respiratory airflow, for example the mouth and/or one or more nostrils. The airway occlusion may be external, for example by using the breathing device 100 described below, which is external to the body and/or internally, for example in the mouth's lumen.

As used herein, a correlation means associating between instantaneous pulmonary properties of a user which are measured at the same respiratory instant and/or stage, mapping and/or binning instantaneous pulmonary properties of a user which are measured at the same respiratory instant and/or stage, and/or scaling and/or normalizing one instantaneous pulmonary property of a user according to another instantaneous pulmonary property which is measured at the same respiratory instant and/or stage.

Reference is now made to FIG. 1, which is a schematic illustration of a system 10 for measurement of respiration parameters, in accordance with embodiments of the present invention. System 10 includes a respiration module 12 and a control unit 14. Respiration module 12 is typically a handheld device that is positionable at a mouth of a user, and is used for inhalation and/or exhalation of air for the purposes of measuring respiration parameters of the user. Respiration module 12 includes a housing 16 having a first end 18 and a second end 20, and a housing body 22 extending from first end 18 to second end 20 and defining a cavity 24 therethrough. Respiration module 12 includes a shutter assembly 32 which can open or close to allow or prevent air flow therethrough and which is controlled by a motor 34. Respiration module may be designed to introduce air flow resistance of less than 1.5 cmH$_2$O/Liter/sec, in accordance with ATS (American Thoracic Society) guidelines for respiratory devices.

Housing 16 may further include at least one pressure measurement component 26 and at least one air flow measurement component 28. Pressure measurement component 26 may be any suitable manometer or sensor for the measurement of absolute pressure with a data rate of at least 500 Hz; and preferably at a data rate of at least 1000 Hz. Such pressure sensors are readily available and may be acquired, for example, from Honeywell Catalog #40PC001B1A. Air flow measurement component 28 may be fabricated for example from an air flow resistive means and a differential pressure manometer, or alternatively from a Pitot tube and a differential pressure manometer. The differential pressure manometer may be any suitable sensor with a data rate of at least 500 Hz; and preferably at a data rate of at least 1000 Hz. Such differential pressure manometers are readily available and may be acquired (for example, from Honeywell Catalog #DC002NDR4. Control unit 14 is in electrical communication with pressure measurement component 26, air flow measurement component 28, and motor 34, which is used for opening and closing of a shutter mechanism, as will be described further below.

Figure 2:
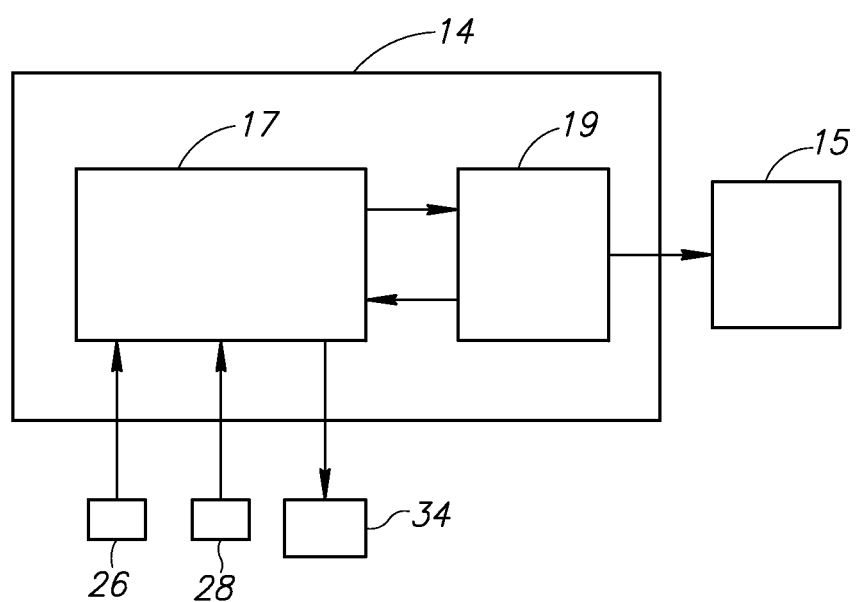
FIG. 2 is a block diagram illustration of a control unit of the system of FIG. 1.

Reference is now made to FIG. 2, which is a block diagram illustration of control unit 14. Control unit 14 may include a converter 17 which converts analog data received from pressure measurement component 26 and air flow measurement component 28 into digital format at a rate of at least once every 2 milliseconds (ms), and preferably at a rate at least once every 1 ms. Converter 17 converts digital signals into commands to motor 34 for shutter assembly 32 to close and to open. Control unit 14 further includes a microprocessor 19 which is programmed to: (a) read digital data of pressure and flow received from the converter 17 in accordance with real-time recording, at a rate commensurate with the converter rate for each data channel and translate this digital data into pressure and flow appropriate units and store them; (b) generate signals which are sent through converter 17 to motor 34 to command the shutter to close or to open, and (c) process above mentioned flow and pressure data in accordance with real time recording, to calculate lung volume and specifically calculate TGV, TLC and RV. Microprocessor 19 also manages a Man-Machine Interface (MMI) that accepts operation commands from an operator and displays results. Control unit 14 may further include a display 15 for displaying the resulting values. Control unit 14 may further include a user input device (e.g., keyboard, touchscreen, mouse, light pin, or other input device) to enter the subject's personal and medical information and to select desired operational modes such as shuttering duration, timing, manual versus automatic operation, calibration procedures, and other modes.

Figure 3:
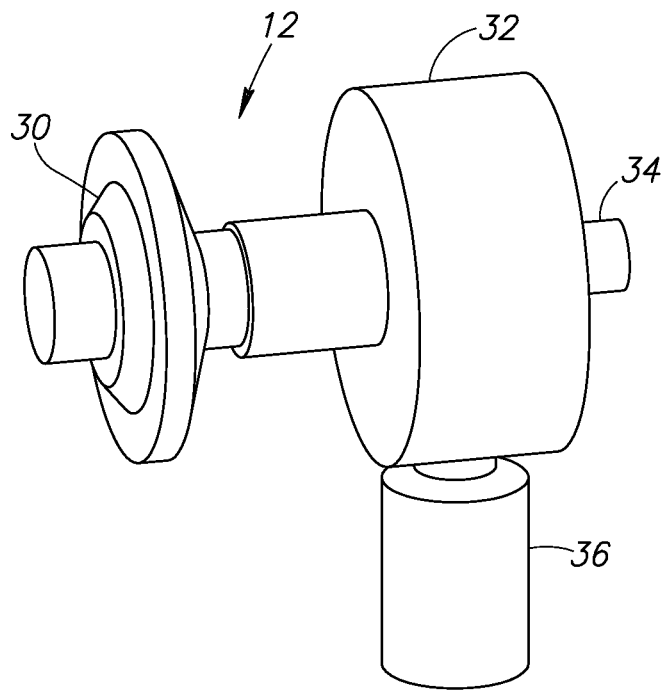
FIG. 3 is a perspective view illustration of a respiration module of the system of FIG. 1, in accordance with one embodiment of the present invention.

Reference is now made to FIG. 3, which is a perspective view illustration of respiration module 12 in accordance with one embodiment of the present invention. Respiration module 12 includes a mouthpiece 30 for placement into a mouth of a user, a shutter assembly 32 attached to (but which may be removable from) mouthpiece 30, a motor 34 for controlling movements of shutter assembly 32, and a flow meter tube 36, which is the air flow resistive means used to calculate air flow parameters. Mouthpiece 30 may be any suitable mouthpiece such as, for example, those available from A-M Systems, Inc. catalog number 156300. Shutter assembly 32 may have several different configurations, some of which will be described in greater detail. Shutter assembly 32 is designed specifically to minimize air displacement during opening and closing thereof. Motor 34 may be any suitable motor such as, for example, a standard solenoid. Alternatively, motor 34 may be any electronically, pneumatically, hydraulically or otherwise operated motor. Finally, flow meter tube 36 is a section of respiration module 12 which is distal to shutter assembly 32. In the present embodiment, flow meter tube 36 is distal to shutter assembly 32 so that measurement of air flow can be taken downstream of the open or closed shutter. However, flow meter tube 36 may also be positioned adjacent to pressure measurement component 26. Flow meter tube 36 may be calibrated in accordance with known methods so as to account for variations in density due to differences in room temperature and body temperature.

Figure 4:
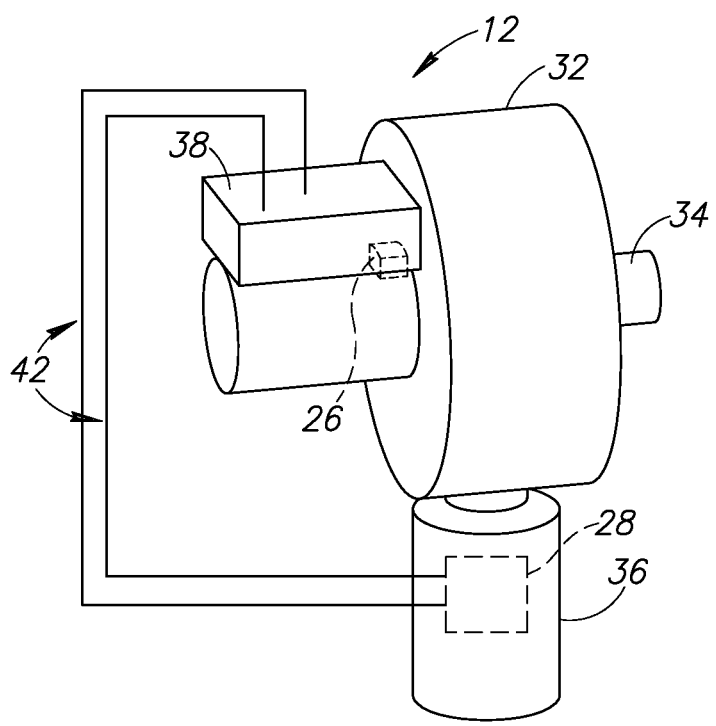
FIG. 4 is a schematic illustration showing the respiration module of FIG. 3 with the addition of electronic components.

Reference is now made to FIG. 4 which is a schematic illustration showing the respiration module 12 of FIG. 3 with the addition of electronic components. An electronics module 38 may be positioned on or next to shutter assembly 32. Electronics module 38 is configured to receive data from pressure and flow measurements and to send the received data to control unit 14 for processing. In some embodiments, control unit 14 is attached to respiration module 12 (and more particularly, to electronics module 38) via wires. In other embodiments, wireless connections may be employed. In the embodiment shown in FIG. 4, pressure measurement component 26 is a pressure sensor positioned in close proximity to mouthpiece 30 and shutter assembly 32 and is within or in direct contact with electronics module 38, and air flow measurement component 28 is a flow meter tube 36 connected via tubes 42 to a differential pressure sensor positioned on or within electronics module 38. Thus, the pressure sensor receives an air pressure signal through an air pipe from shutter assembly 32 from a point between mouthpiece 30 and shutter assembly 32. The pressure sensor outputs an electrical signal proportional to the air pressure in the pipe (relative to the surrounding atmospheric pressure). The differential pressure sensor accepts two air pipes from flow meter tube 36. The differential pressure sensor outputs an electronic signal proportional to the difference in pressure between the two pipes, which may be converted into a flow signal. It should be readily apparent that the invention is not limited to the embodiment shown herein and that in some embodiments, electronics module 38 may be positioned in a different location.

Shutter assembly 32 is used for breaking a stream of inhaled or exhaled air, located within cavity 24. Shutter assembly 32 is configured to operate quietly so as not to create any reflexes or undesired responses by the subject, thereby avoiding inaccuracies of measurement. More importantly, shutter assembly 32 is configured to operate quickly, both in terms of its shutting speed (i.e., the time it takes for the shutter to go from an open state to a closed state and vice versa) and in terms of its shutting duration (i.e., the period of time for which the shutter is closed). The shutting speed is in some embodiments less than 10 ms, preferably less than 5 ms, and more preferably less than 2 ms. The shutting duration is in some embodiments less than 2 seconds and preferably less than 100 ms. This fast paced shutting speed and shutting duration are key features in the present invention to provide the accuracy and reliability of the measurement of TGV, TLC and RV. The need for high speed operation of shutter assembly 32 and high rate of data acquisition (as described above with reference to control unit 14) results from the typical response time of the lungs to abrupt occlusion of the airways while breathing. The response time of the lungs of a human being is in the order of ms to tens of ms, and accurate recording of the details of the response of the lungs to such abrupt occlusion is essential for accurate calculation of the internal volume of the lungs.

Figure 5A:
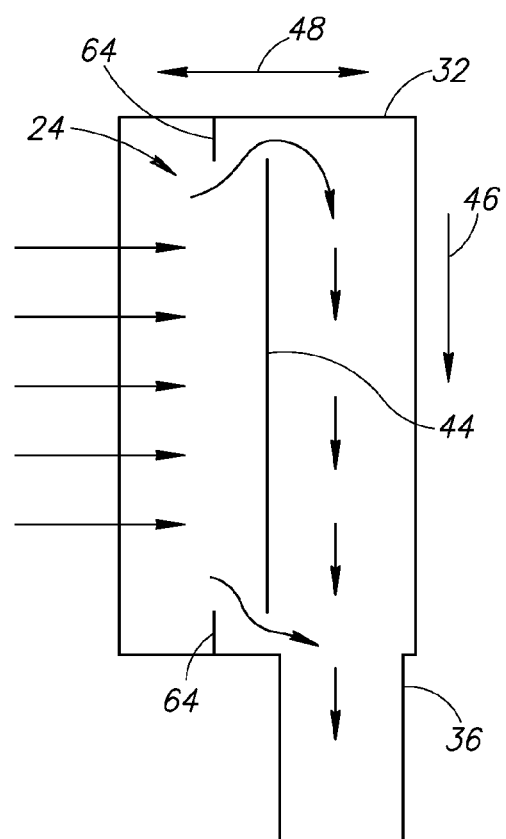
FIGS. 5A and 5B are schematic illustrations showing a movable portion positioned within a shutter assembly which is configured to move back and forth, shown in an open configuration and a sealed configuration, respectively.
Figure 5B:
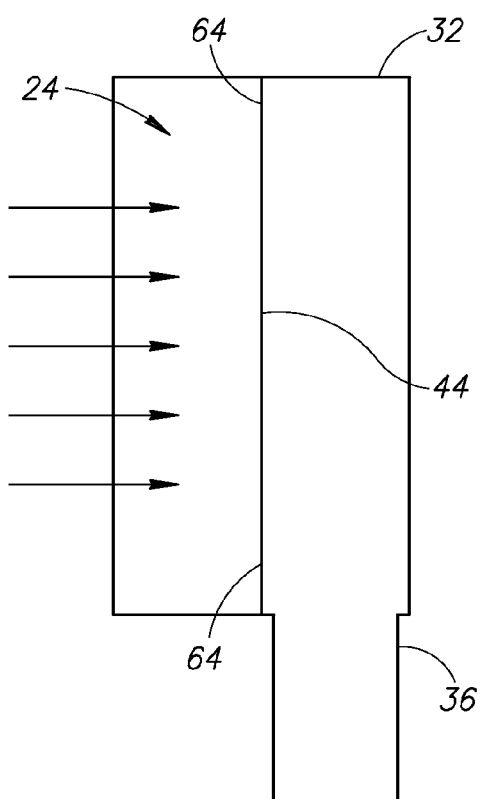

In addition to high speed, shutter assembly 32 is also configured to perform occlusion of cavity 24 with minimum, and preferably without any, displacement of air that may be recorded by the pressure sensor or the flow sensor. In order to provide rapid shutter movement with minimal air displacement, shutter assembly 32, as well as other embodiments of shutter assembly in accordance with the present invention, is designed so that the open/close movement of the shutter is substantially orthogonal to the direction of air flow being measured. Thus, in one embodiment, as shown in FIGS. 5A and 5B, a movable portion 44 is positioned within shutter assembly 32 and is configured to move back and forth in a first direction, as shown by arrow 48. A fixed portion 64 may be present as well, wherein when movable portion 44 is in an open position, movable portion 44 does not contact fixed portion 64 so as to allow for air flow, and when movable portion is in a closed position, movable portion 44 is in contact with fixed portion 64 so as to seal any air flow pathways. Air flow which enters shutter assembly 32 is configured to move in a direction which is substantially orthogonal to the movement of movable portion 44, as shown by arrow 46. In FIG. 5A, shutter assembly 32 is shown in an open configuration, wherein air flow is possible; in FIG. 5B, shutter assembly 32 is shown in a closed configuration, wherein air flow is stopped due to the movement of movable portion 44 and contact of movable portion 44 with fixed portion 64. A more detailed example of this type of configuration will be described below.

Figure 6:
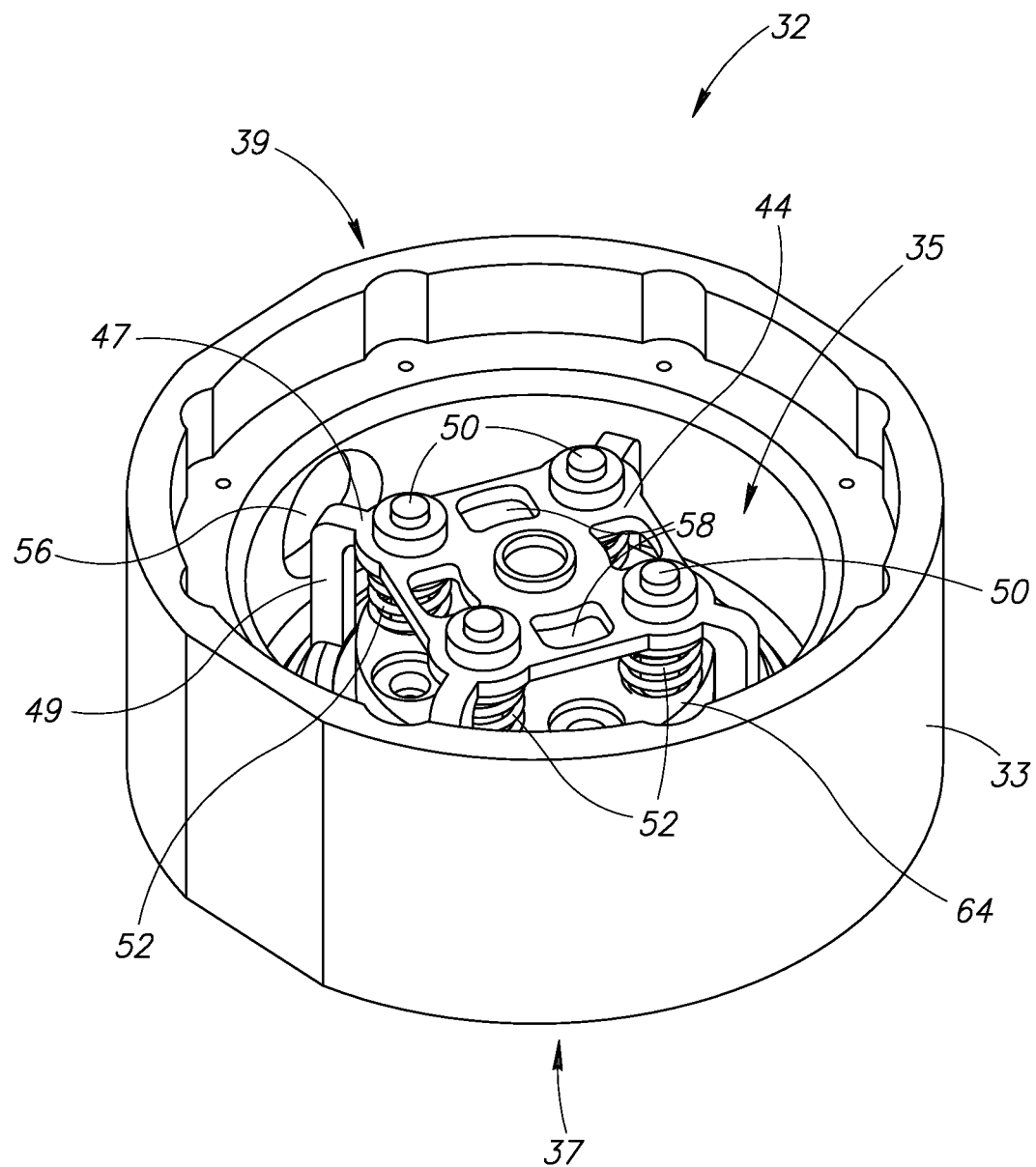
FIG. 6 is a perspective illustration of an internal view of a portion of a shutter assembly, in accordance with embodiments of the present invention.

Reference is now made to FIG. 6, which is a perspective illustration of an internal view of a portion of shutter assembly 32, in accordance with embodiments of the present invention. Shutter assembly 32 includes a shutter assembly housing 33 defining a chamber 35. Chamber 35 is a portion of cavity 24 of respiration module 12, described above with reference to FIG. 1. However, chamber 35 refers to the portion of cavity 24 which is part of shutter assembly 32. Chamber 35 has a proximal end 37, which is the end closest to mouthpiece 30 when mouthpiece is present and which is proximal to movable portion 44 of shutter assembly 32, and a distal end 39, which is distal to movable portion 44 and which is closed to air flow. Thus, air flows from proximal end 37 to distal end 39, but is configured to exit chamber 35 via an outlet 56 positioned along a wall of chamber 35. A fixed portion 64 is positioned at proximal end 37 of chamber 35. Movable portion 44 includes a flat surface 47, a sealing portion 60 (not shown) and a connecting portion 54 connecting flat surface 47 to sealing portion. Movable portion 44 is positioned adjacent to and is movable with respect to fixed portion 64 via leading pins 50 and springs 52 positioned there between.

Figure 7A:
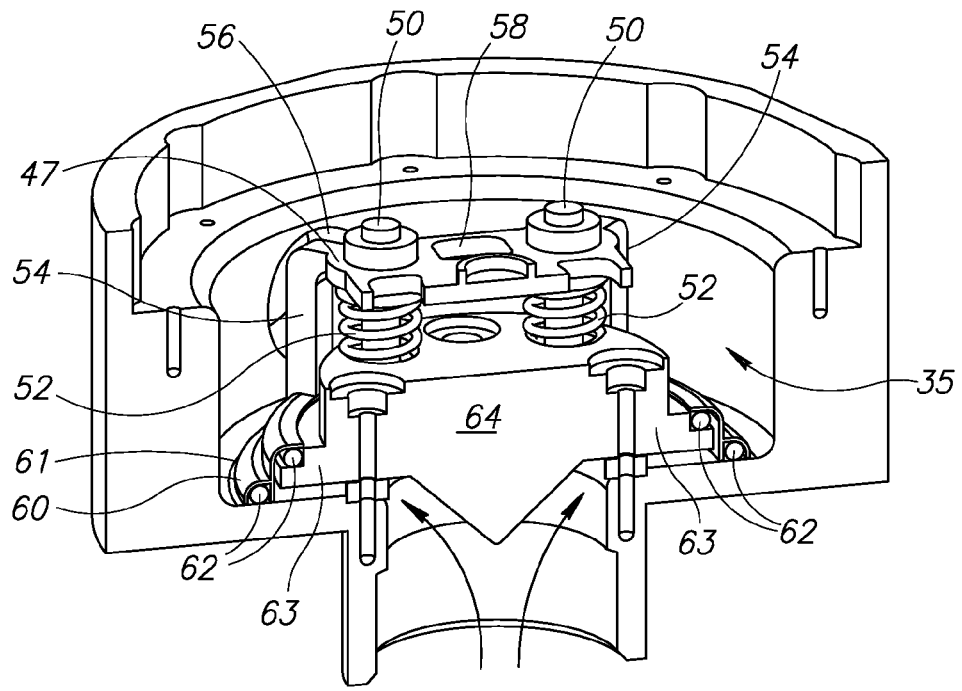
FIG. 7A and FIG. 7B are partially cut-away perspective illustrations of the shutter assembly of FIG. 6, shown in a sealed configuration and an open configuration, respectively.
Figure 7B:
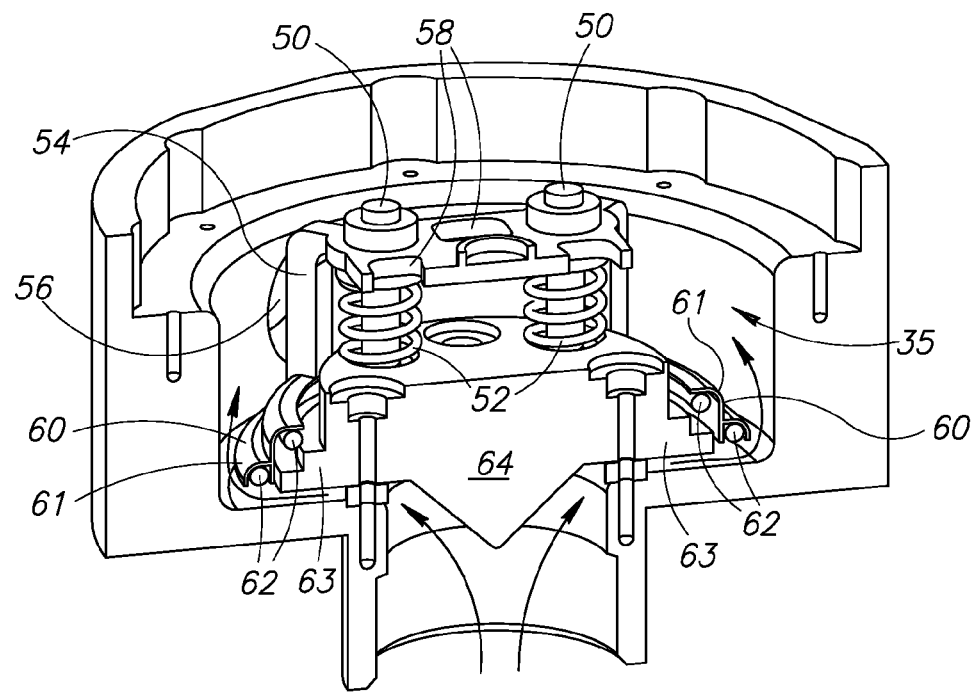

Reference is now made to FIG. 7A and FIG. 7B, which are partially cut-away perspective illustrations of shutter assembly 32 in a sealed configuration and an open configuration, respectively. As shown in FIG. 7A, sealing portion 60 of movable portion 44 includes a circular compartment 61 within which may be positioned a set of O-rings 62. One of O-rings 62 may be positioned against a chamber floor and the other one of O-rings 62 may be positioned against a stair 63 of fixed portion 64. When movable portion 44 is pushed towards fixed portion 64 (via motor 34 such as a solenoid, for example) as shown in FIG. 7A, circular compartment 61 fully encloses O-rings 62, thus preventing air flow. When movable portion 44 is released, springs 52 push movable portion 44 away from fixed portion 64, resulting in air space between O-rings 62 and the chamber floor. Thus, air can flow into chamber 35, and out through outlet 56 located on a wall of chamber 35. It is a feature of the present invention that the shutter assembly allows for minimal air displacement. This may be accomplished, for example, by providing a small area of movement which can be used to displace a large amount of air and which has available a large "flow area", defined as an area available for air flow. In the present example, this feature can be seen as follows. The area through which air flows is the area of sealing in the vicinity of the O-rings, and is substantially proportional to the circumference of the O-rings. Moreover, since flat surface 47 is full of openings 58, movement of movable portion 44 has a relatively small surface area. Thus, movements are contained to a small surface area, while allowing for a relatively large flow area in a post-shutter component of cavity 24.

Figure 8A:
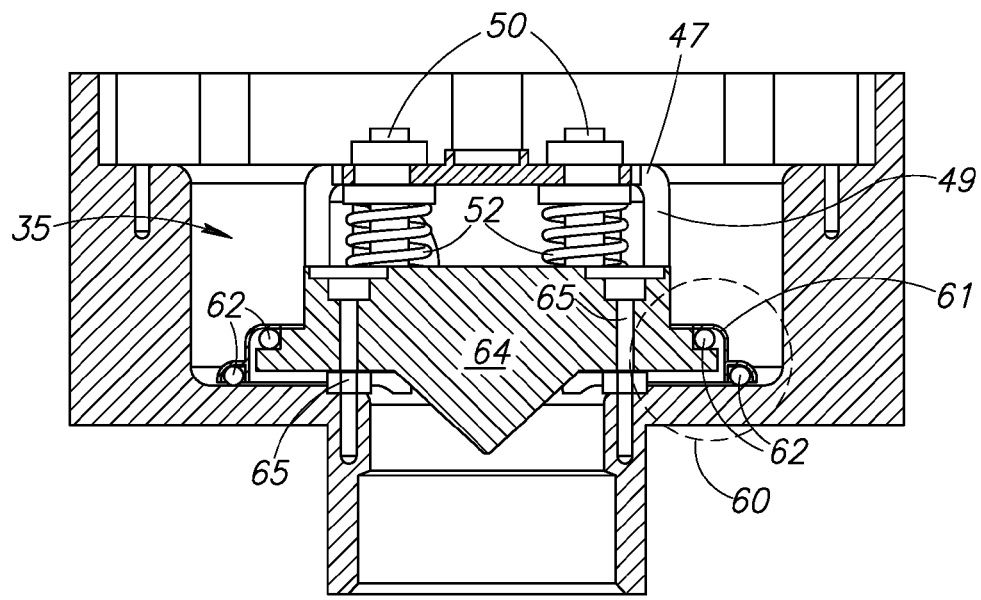
FIG. 8A is a cross sectional illustration of a chamber of the shutter assembly of FIG. 6.
Figure 8B:
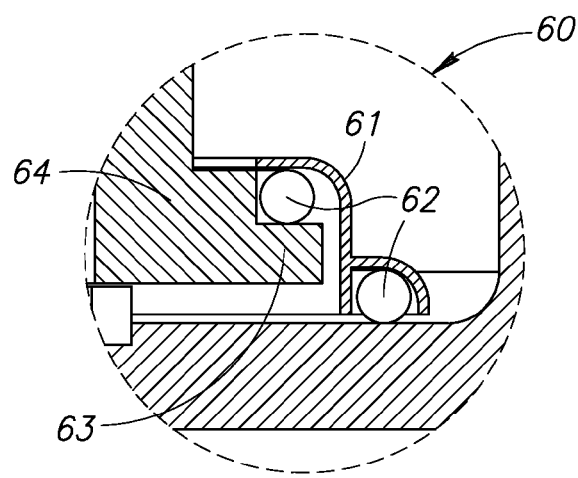
FIG. 8B is a cross sectional illustration showing a sealing portion of the shutter assembly of FIG. 8A in greater detail.

Reference is now made to FIG. 8A, which is a cross sectional illustration of chamber 35 of shutter assembly 32. Fixed portion 64 is fixed to chamber 35 via screws 65 or other fixation means. Flat portion 47, connecting portion 54 and sealing portion 60 of movable portion 44 are all visible in cross section. Springs 52 positioned on pins 50 allow for movement of movable portion 44 with respect to fixed portion 64. Reference is now made to FIG. 8B, which is a cross sectional illustration showing sealing portion 60 in greater detail. Sealing portion 60 includes circular compartment 61 with O-rings 62 positioned therein. O-rings 62 are positioned on fixed portion 64 and on the floor of chamber 35.

Figure 9A:
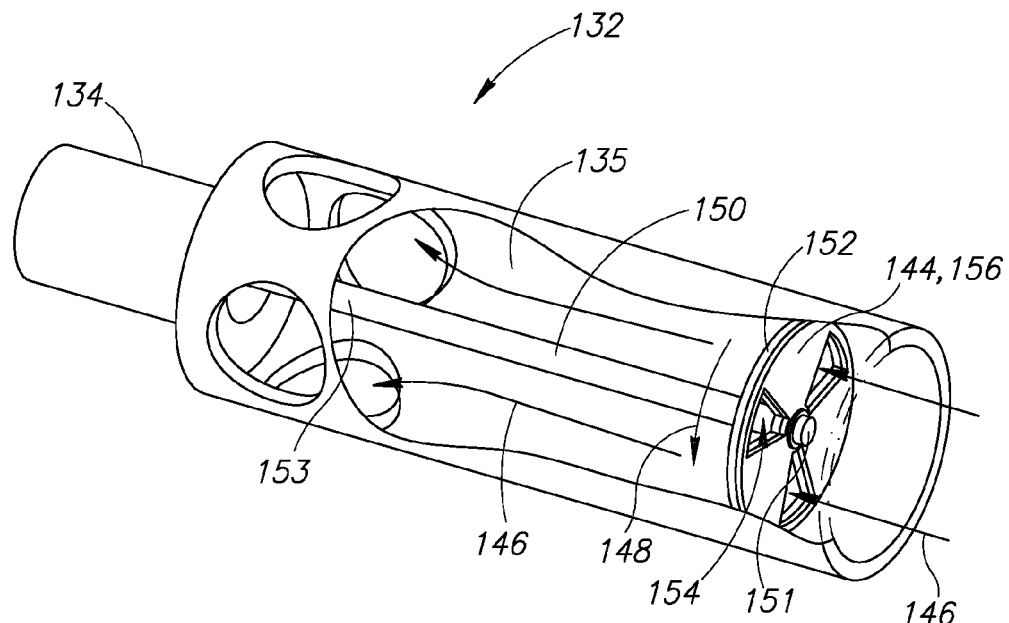
FIG. 9A is a perspective illustration of a shutter assembly in accordance with additional embodiments of the present invention.

Reference is now made to FIG. 9A, which is a perspective illustration of a shutter assembly 132 in accordance with additional embodiments of the present invention. Shutter assembly 132 includes a chamber 135 for air flow wherein chamber 135 is substantially cylindrical in shape. A motor 134 is positioned at a first end of chamber 135 and is attached to a rotatable shaft 150 running through a center of chamber 135. Motor 134 is configured to provide rotational movements to rotatable shaft 150. Rotatable shaft 150 includes a proximal end 151 and a distal end 153. Motor 134 may be attached to distal end 153, although other locations are possible as well. Motor 134 may be any motor suitable for providing such movements, such as a step motor, for example. At proximal end 151 of rotatable shaft 150, there is positioned a disk 152 having openings 154 for air flow. Disk 152 fits within chamber 135 such that air cannot flow around the sides of disk 152, but can only flow through openings 154. A movable portion 144 comprises a rotating shutter 156 attached to proximal end 151 of rotatable shaft 152 and is configured to rotate upon activation of motor 134. Rotation of rotating shutter 156 causes openings 154 to be closed, thus blocking air flow. A direction of air flow, shown by arrows 146 is substantially orthogonal to a direction of rotation of rotating shutter 156, depicted by arrow 148. Moreover, a cross-sectional surface area of movable portion 144 in the direction of movement of movable portion 144 is equivalent to the thickness of the rotating disk, since movement occurs in the rotational plane. This surface area is much smaller than the flow area just past rotating shutter 156. In one embodiment, disk 152 may be rotatable in a direction opposite to the rotation of rotating shutter 156. This provides faster shuttering speeds than one moving part.

Figure 9B:
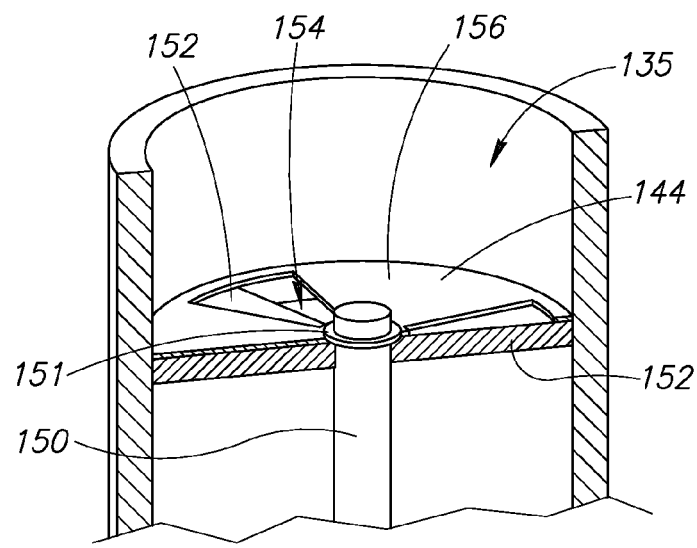
FIG. 9B is a partially cut away view of the shutter assembly of FIG. 9A.

Reference is now made to FIG. 9B, which is a partially cut away view of disk 152, openings 154, and movable portion 144—which is rotating shutter 156.

Figure 10:
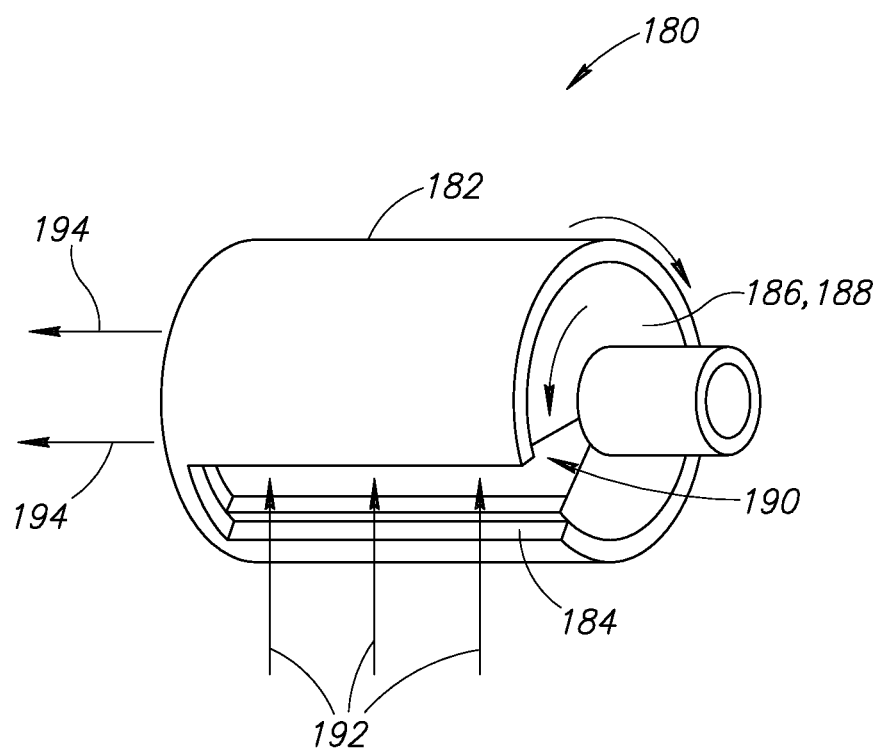
FIG. 10 is a perspective illustration of a shutter assembly in accordance with yet additional embodiments of the present invention.

Reference is now made to FIG. 10, which is a perspective illustration of a shutter assembly 180, in accordance with yet additional embodiments of the present invention. Shutter assembly 180 includes an outer cylinder 182 with an outer slit 184 along at least a portion of a length thereof. Outer slit 184 is preferably long and narrow. A movable portion 186 includes an inner rotatable cylinder 188 having an inner slit 190 along at least a portion of a length thereof. Inner rotatable cylinder 188 is positioned within said outer cylinder 182 such that air is prevented from flowing between outer cylinder 182 and inner rotatable cylinder 188. When outer slit 184 and inner slit 190 are aligned, an opening is created for movement of air flow in a direction of arrows 192 and arrows 194. Inner rotatable cylinder 188 rotates in one direction. In some embodiments, outer cylinder 182 may rotate as well, in an opposite direction of inner rotatable cylinder 188. This provides faster shuttering speeds than one moving part.

In addition, the shape of inner slit 190 and outer slit 184 may be configured so as to minimize shuttering time while maximizing air flow. For this reason, a rectangular shape may be used, wherein a narrow width allows for rapid opening and closing, while the length provides a relatively large flow area.

Methods of Calculation

The basic concept of the methods of the present invention is that estimation of RV, TLC and TGV may be done based on measurements of the change of volume of gas in the lungs, $\Delta V$, and the accompanying pressure change in the lungs, $\Delta P$, during a short interruption to the breathing of the patient. The interruption is achieved by a quick shutter that shuts the mouth of the patient for a short period of time, either during exhalation or during inhalation. Devices which may be used for quick shuttering with minimal air displacement which may be used in the methods of the present invention are described above with reference to FIGS. 1-10. Quick shuttering is critical in order to obtain resolution necessary to discern parameters which may be measured to obtain volume values.

The first parameter which must be obtained is $V_0$, the instantaneous volume of gas in the lungs at a given point in time. For the purposes of the present invention, $V_0$ is taken as the volume of gas within the lungs upon the shutter event. $V_0$ may be obtained in many different ways. Two different methods for obtaining $V_0$ are described below as Method A and Method B.

Once $V_0$ is obtained, the following method may be used to obtain TGV.

Figure 11:
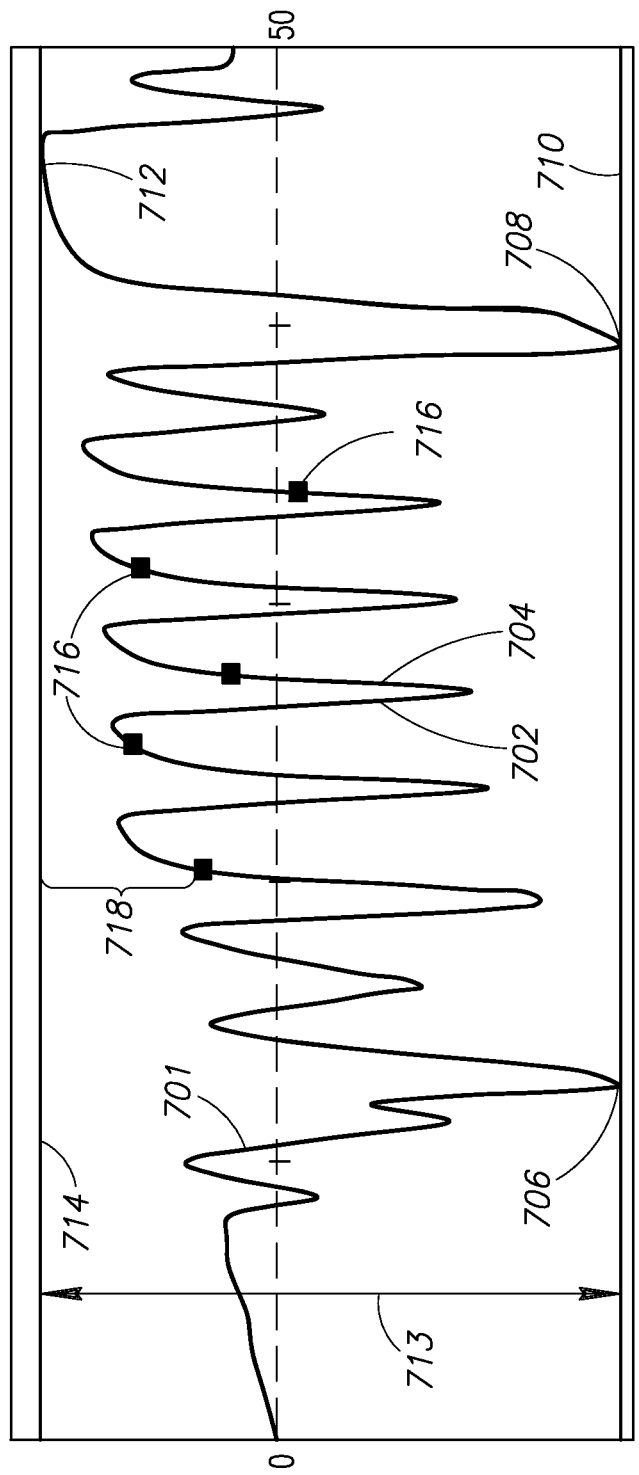
FIG. 11 is a graphical illustration showing volume changes over the course of a series of inspirations and expirations.

Reference is now made to FIG. 11, which is a graphical illustration showing a volume curve 701 over the course of a series of inspirations and expirations, which are not necessarily tidal respirations. Inspirations 702 are shown on the curve going from top to bottom, and expirations 704 are shown going from bottom to top. TLC is determined by a first full inspiration 706 and a second full inspiration 708 taken to full capacity. Thus, a patient is asked to fully inhale at least twice in each session in order to determine TLC level 710, preferably at the beginning and at the end of each measurement session, to account for potential drifting of volume along the series of inspirations and expirations exercised by the subject. TLC level 710 is obtained directly from these two full inspirations. Following second full inspiration 708, the patient is asked to exhale fully in order to obtain a full expiration 712. RV level 714 is obtained directly from full expiration 712, and in parallel to TLC level 710. The amplitude from RV level 714 to TLC level 710 equals VC 713.

At several points along the volume curve 701, a shutter event is initiated, and $V_0$ is calculated by one of Methods A or B. Shutter events are shown in FIG. 11 as points 716. Each of the shutter events may take place at different points along either an inspiration 702 or expiration 704 cycle. The difference in volume between $V_0$ measured at a shutter event 716 and RV level 714, is $RV_{ADJ}$ 718, as computed at that specific timing. $RV_{ADJ}$ 718 stands for all of the volume of air that a subject would have maximally expired during a cycle should the subject have been asked to maximally expire. Thus, once $V_0$ is calculated by one of methods A or B per a single shutter event 716, RV is obtained as follows:

$$RV = V0 - RV_{ADJ}$$

$RV_{ADJ}$ 718 may be large or small depending on when the shutter event is initiated. However, it is necessarily smaller than VC 713, which equals the difference between TLC level 710 and RV level 714. Once RV has been calculated, TLC can be obtained as follows:

$$TLC = RV + VC$$

and TGV can be obtained by:

$$TGV = RV + ERV$$

where ERV (Expiratory Reserve Volume), is obtained by a standard spirometry measurement.

Methods A and B for determination of $V_0$ will now be described.

Method A:

Starting from the ideal gas law $$PV = nkT$$

where P is the pressure, V the volume, n the number of gas molecules and T the gas temperature, we obtain for the gas in the lungs which is maintained at a fixed temperature (also known as Boyle's Law)

$$P_0 V_0 = \text{Const.}$$

If the lungs contract by some volume $\Delta V$, then the pressure in the lungs rises by an amount $\Delta P$, so that $$P_0 V_0 = (V_0 - \Delta V)(P_0 + \Delta P)$$

which yields, $$V_0 = \Delta V / \Delta P (P_0 + \Delta P)$$

If the changes in volume and pressure are small compared to the absolute values $V_0$ and $P_0$, $$V_0 = P_0 \frac{\Delta V}{\Delta P}$$

Hence, by measuring the change in lung volume and the change in the pressure inside the lungs, and knowing the base pressure—which approximates the atmospheric pressure—the internal volume of the lungs at the moment of shutting, $V_0$, may be extracted.

Figure 12:
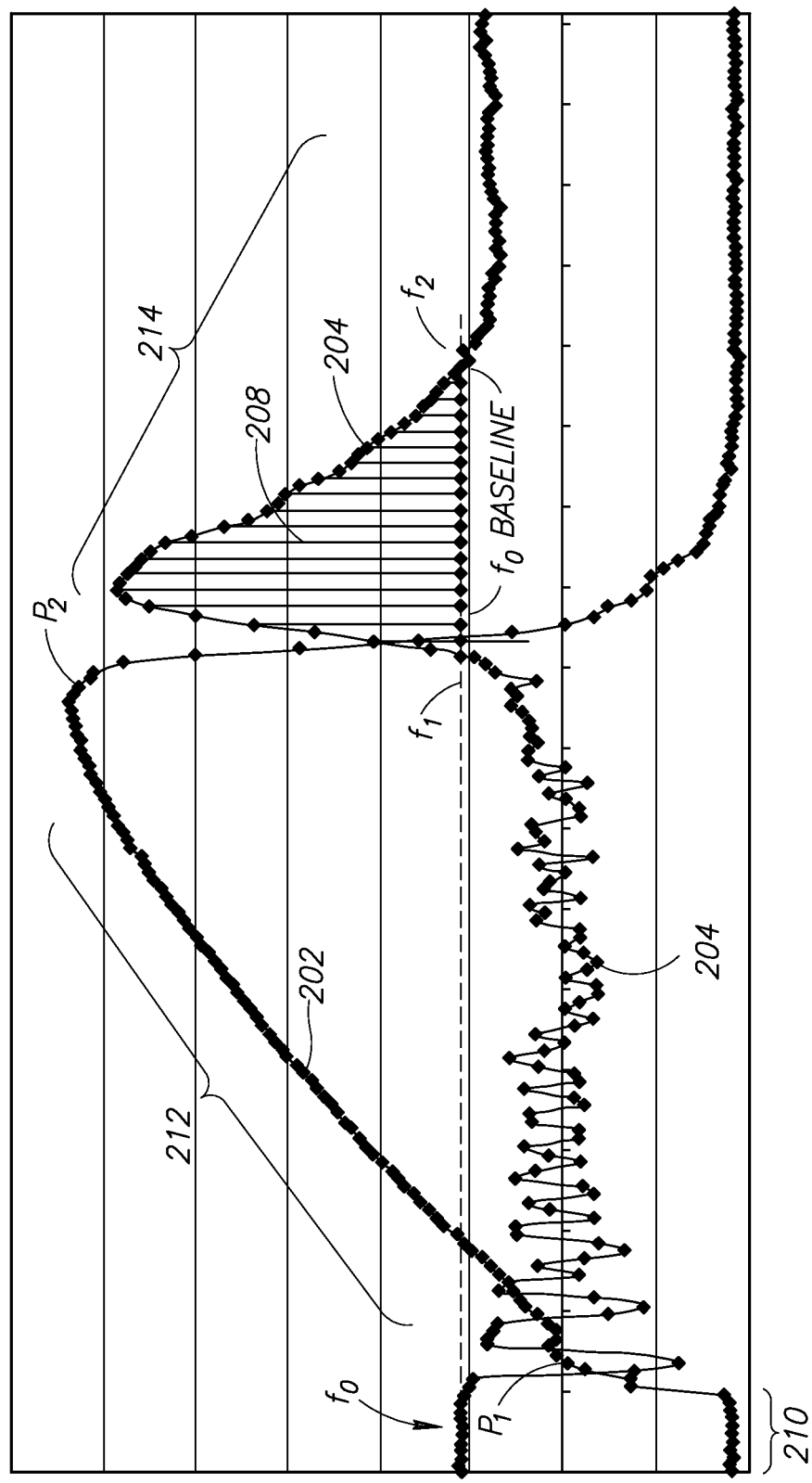
FIG. 12 is a graphical illustration of flow and pressure curves over time obtained during exhalation with a shutter closing episode, showing features used in a method of calculating $V_0$ in accordance with embodiments of the present invention.

Reference is now made to FIG. 12, which is a graphical illustration of flow and pressure curves over time obtained during exhalation with a shutter closing episode. It should be readily apparent that the scale of FIG. 12 is much smaller than the scale of FIG. 11, as FIG. 12 is a depiction of one single shutter event 716 as it relates to FIG. 11. A pre-shutter period 210 is followed by a shutter event 212, which is followed by a post-shutter period 214. Pressure is shown on the upper curve 202 and flow is shown on lower curve 204. Flow decreases to zero during shutter event 212, then rises again, and forms an "overshoot" which relaxes back to the normal flow rate, as the extra volume of gas that was compressed in the lungs during the shutter event is exhaled. The pressure rises sharply when the shutter is closed and then may rise further to a peak just before the shutter opens. Also apparent in FIG. 12 is that during shutter event 212, a small amount of air (compared to $\Delta V$) may escape through the shutter because of less than ideal shutting. This amount of air, referred to as the Escaped Volume and denoted as $\Delta V_{Esc}$ is readily calculated by integrating the flow over shutter event 212. The correction that the escaped volume introduces into the formula for calculating $V_0$ $$V_0 = P_0 \frac{\Delta V - \Delta V_{Esc}}{\Delta P}.$$

A method for determining $V_0$, in accordance with an embodiment of the present invention is described. According to this method, referred to herein as method A, the change in pressure ($\Delta P = P_2 - P_1$) is measured during the shutter event (i.e., during the time the shutter is closed), and the change in volume ($\Delta V$) is measured after the shutter is opened. According to this method, the accumulated gas which generates the pressure rise during the shutting is released and measured after the shutter opens. Thus, it is important to quantify the volume which is released due to the shutter event only, and to distinguish this released volume from the volume changes which occur due to regular expiration.

Figure 13:
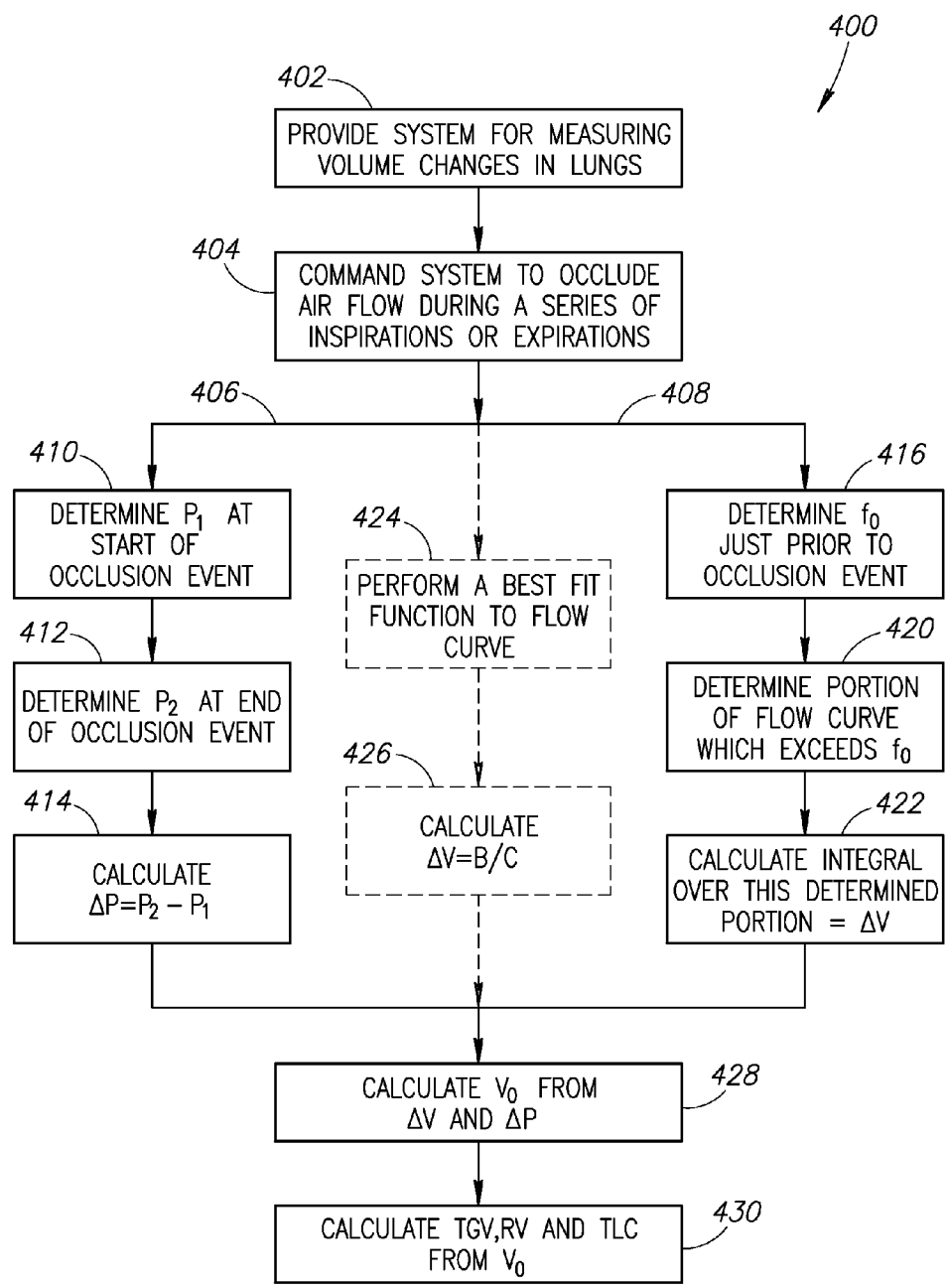
FIG. 13 is a flow chart diagram illustration of the method of FIG. 12 and a method of calculating TGV, RV, and TLC in accordance with embodiments of the present invention.

Reference is now made to FIG. 13, which is a flow chart diagram illustration of a method 400 of calculating TGV, in accordance with embodiments of the present invention. First, a system for measuring volume changes in the lungs is provided (step 402). The system includes a respiratory module with means to occlude air flow. Next, a command is given (step 404) to the system to occlude air flow within the respiratory module of the system at various stages of inspiration and/or expiration. The command may be given manually or automatically, or as a combination of both. For a given occlusion event, change in pressure ($\Delta P$) during the occlusion event is calculated (step 406) and change in volume ($\Delta V$) due to released volume due to the occlusion event is calculated (step 408).

Calculation of $\Delta P$ can be done as follows. First, a first pressure $P_1$ is determined (step 410), wherein $P_1$ represents the pressure at the beginning of the occlusion event. $P_1$ is generally determined at a point at which the pressure curve has finished its initial sharp slope and begins a more moderate slope following closing of the shutter, also referred hereinafter the "knee region", as to reflect the general shape of the curve at P1. Next, a second pressure $P_2$ is determined (step 412), wherein $P_2$ represents the pressure at the moment at which the shutter starts to open. Next, the difference between second pressure $P_2$ and first pressure $P_1$ is calculated (step 414), resulting in a value for $\Delta P$.

Calculation of $\Delta V$ can be done as follows. First, $f_0$ is determined (step 416), wherein $f_0$ represents the flow just prior to the occlusion event. This can be done by determining an average of flow measurement data over a range of up to 20 ms prior to closing of the shutter or may be measured via one appropriate data point in the flow measurement raw data. Next, the portion of the flow curve which exceeds $f_0$ is determined (step 420). A baseline, referred to as the $f_0$ baseline, is shown in FIG. 12, stretching between $f_1$ and $f_2$. Finally, the integral of the portion of the flow curve determined in step 420 is calculated (step 422), resulting in $\Delta V$, as illustrated in FIG. 12 by the darkened area 208.

In an alternative embodiment, calculation of $\Delta V$ is done by performing (step 424) a best fit of a function, for example, of the form $A+B*\exp(-C*t)$, to the flow curve, over the range that starts at least 5 ms after the shutter opens and the flow curve starts to rise, and ends at most 100 ms after the shutter opens, where t is the time measured at the point in time when the shutter opens and the flow curve starts to rise, and A, B and C are the fit parameters. Then $\Delta V = B/C$ is calculated (step 426). It should be noted that the time period over which measurements are taken may vary depending on shutter event duration or other parameters. It will be appreciated that the invention is not limited to the methods described herein, and that any method which calculates an excess of air which is exhaled immediately following the opening of the shutter is included within the scope of the present invention. Moreover, the methods of present invention are not dependent on specific shutter event duration parameters. Any parameters which allow for the calculation of the values in accordance with the methods presented herein are within the scope of the present invention.

Once $\Delta V$ and $\Delta P$ are obtained, $V_0$ is calculated (step 428) from $\Delta V$ and $\Delta P$, in accordance with the equation $V_0 = (P_0 + \Delta P) \Delta V / \Delta P$. Finally, RV, TLC and TGV are calculated (step 430) based on $V_0$, as described above with reference to FIG. 11.

Determination of $P_1$ is critical. However, its exact location may be obscured by oscillations on the pressure signal immediately following shutter closing for as long as 30 ms. In one embodiment, determination of $P_1$ is done by performing an extrapolation of the smooth portion of the pressure signal, backwards to the "knee region", hence overcoming the problem of the oscillations in the immediate vicinity of $P_1$.

Figure 14:
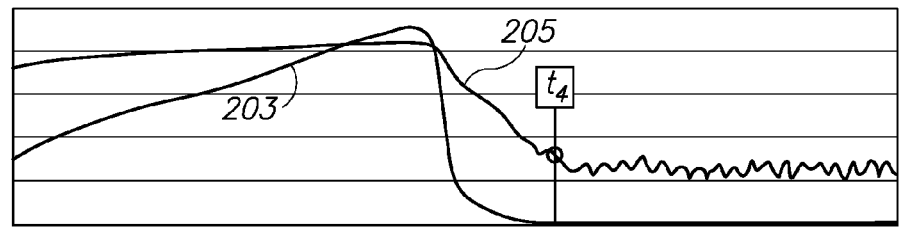
FIG. 14 is a graphical illustration showing a method of measurement of ΔV.

Reference is now made to FIG. 14, which is a graphical illustration showing an alternative measurement of $\Delta V$. According to this method, $\Delta V$ is obtained by integrating the flow curve above the $f_0$ baseline, as described above in FIG. 12. However, the integration is done from the point where the flow crosses $f_0$ when the shutter opens until an identifiable point $t_4$, which is typically different from the point in time when the flow crosses again the level of $f_0$ on its decrease.

The point $t_4$ is identified on the pressure curve, as the point where exponential decrease of the pressure, associated with the relief of excess of air from the lungs, has stopped. This point may be identified by viewing the pressure curve on a logarithmic scale as in FIG. 14, and identifying a knee-shaped pattern on the curve, marked on the graph as $t_4$. In FIG. 14, the pressure curve is shown on a linear scale 203 and on a logarithmic scale 205. The point $t_4$ is marked as the end of the linear decrease of the logarithmic scale 205. It should be noted that the baseline can be varied by assuming that the normal motion of the lungs accelerates linearly from an initial flow rate proportional to $f_0$ to the flow rate at $t_4$.

Example Using Method A:

An example of a measurement taken by measuring $\Delta P$ and $\Delta V$ wherein $\Delta P$ is measured during the time the shutter is closed, and $\Delta V$ is measured during the time the shutter is open, in accordance with method A is now given. In the current example, a patient was requested to inhale fully to the TLC level, and then to immediately exhale fully to the RV level, once at the beginning of the measurement and once at the end of the measurement.

In this example, $RV_{ADJ}$ 718 (FIG. 11)=0.81 L. On pressure curve 202 (FIG. 12) a smooth function is fitted to the curve along the first 50 ms and extrapolated backwards to the point it crosses the pressure curve, $P_1$. $P_2$ is noted at the instant just prior to the opening of the shutter and the sharp decrease of the pressure signal. In this example $P_1$=3.99 mmHg and $P_2$=15.20 mmHg, hence $\Delta P$=11.21 mmHg. The excess volume which is released after the shutter opening $\Delta V$, is the area under the flow curve and above $f_0$ baseline, which in this example stands for $\Delta V$=0.042 L.

From here $V_0$ according to Method A is readily calculated as:

$$V_{0[A]} = P_0 \frac{\Delta V}{\Delta P} = 760 \frac{0.042}{11.21} = 2.84L$$

Accordingly, RV is found to be $$RV_{[A]} = V_{0[A]} - RV_{ADJ} = 2.84 - 0.81 = 2.03L$$

Method B:

The basic theory behind method B is as follows: Starting from $$P_0 V_0 = \text{Const.},$$

assuming P and V are homogeneous and quasi steady, differentiation over time provides:

$$P_0 \frac{dV}{dt} + V_0 \frac{dP}{dt} = 0$$

where $P_0$ and $V_0$ are the pressure and volume of the system at any given moment. Now $$\frac{dV}{dt}$$

is the rate of contraction of the lungs' volume, and if we assume continuity of motion over the short period of time of the shutter closing, we conclude that it is equal to the flow rate from the mouth just prior to the closing of the shutter. Hence rearranging the last equation gives $$V_0 = -P_0 \frac{dV/dt}{dP/dt} = \frac{P_0 \cdot f_0}{dP/dt}$$

where $V_0$ is the lungs' volume, $P_0$ approximates the atmospheric pressure, $f_0$ is the flow rate just prior to the shutter closing and $$\frac{dP}{dt}$$

is the slope of pressure rise (as a function of time) just after the shutter closing.

The rate of change of the volume of the lungs is equal to $f_0$, the flow just prior to the closing of the shutter, and the rate of change of the pressure is measured right after the shutter closes. Assuming continuity in the physical movement of body tissues during breathing, the lungs, which contract at a roughly constant pace during breathing, will continue to contract at the same pace for a short time interval after the shutter closes, and hence contribute to the rise in pressure.

Figure 15:
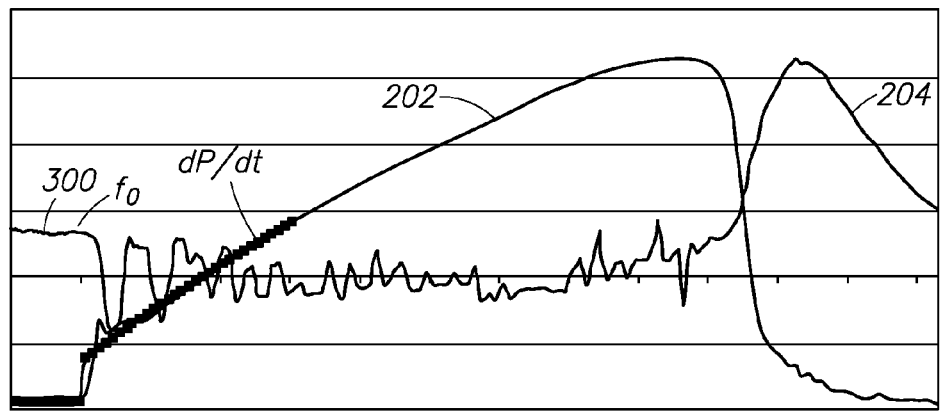
FIG. 15 is a graphical illustration of a flow curve and a pressure curve over time obtained during exhalation with a shutter closing episode, showing features used in another method of calculating $V_0$ in accordance with embodiments of the present invention.

Reference is now made to FIG. 15, which is a graphical illustration of a flow curve 204 and a pressure curve 202 over time obtained during exhalation with a shutter closing episode. According to this method, referred to herein as method B, the rate of change in pressure (dP/dt) is determined during the shutter event (i.e., during the time the shutter is closed), and the instantaneous volume ($V_0$) is calculated rather than obtained by directly measuring a change of volume, $\Delta V$.

Figure 16:
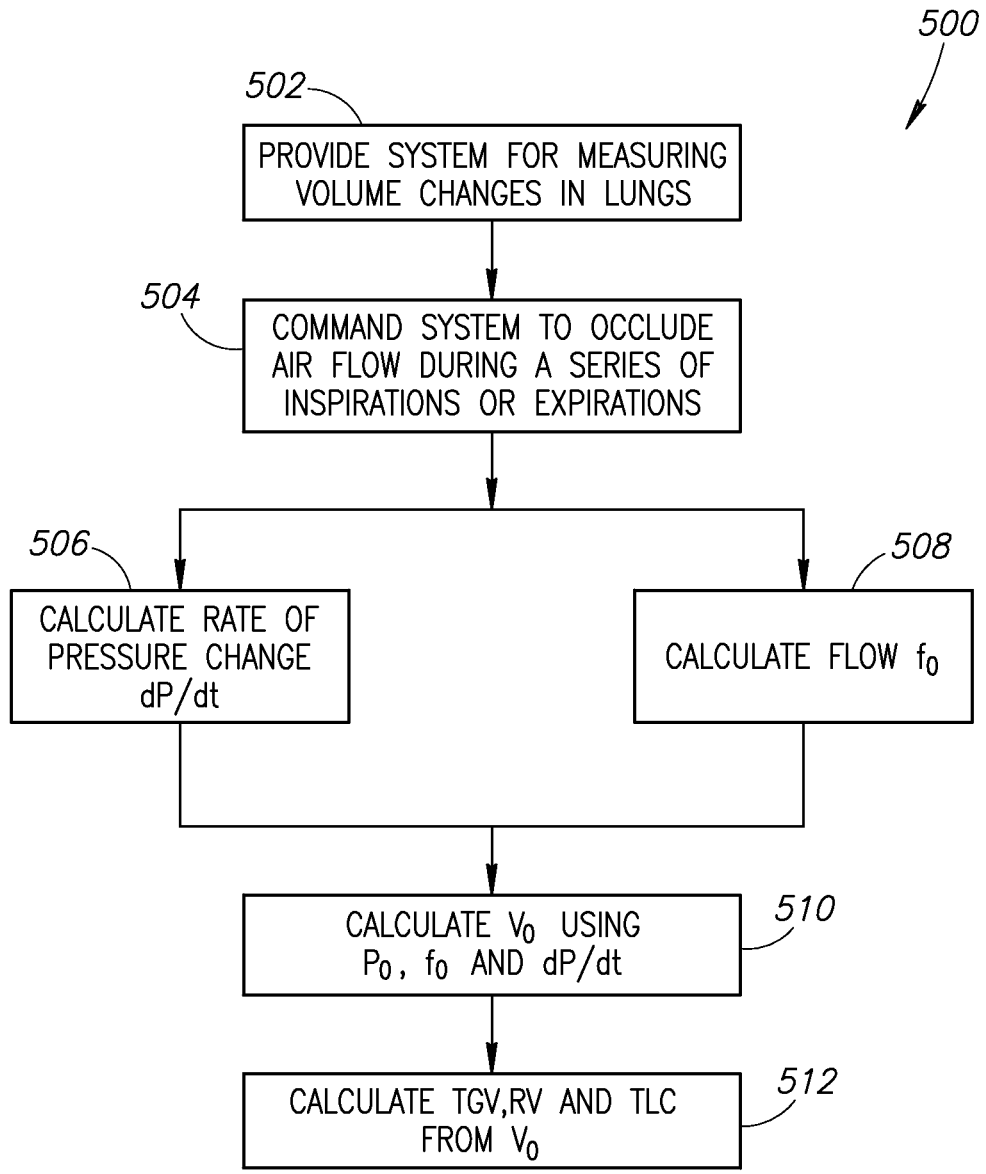
FIG. 16 is a flow chart diagram illustration of the method of FIG. 16 and a method of calculating TGV, RV and TLC in accordance with embodiments of the present invention.

Reference is now made to FIG. 16, which is a flow chart diagram illustration of a method 500 of calculating TGV, RV and TLC in accordance with embodiments of the present invention. First, a system for measuring volume changes in the lungs is provided (step 502). The system includes a respiratory module with means to occlude air flow. Next, a command is given (step 504) to the system to occlude air flow within the respiratory module of the system at various stages of inspiration and/or expiration. The command may be given manually or automatically, or as a combination of both. For a given occlusion event, rate of pressure change (dP/dt) during the occlusion event is calculated (step 506). dP/dt is determined within the first 100 ms following shutter occlusion. During that lapse of time, intrapulmonary pressure generally climbs in comparison to pre-shutter closure level. Rate of volume change (dV/dt) is flow ($f_0$), which is determined (step 508) as described above with reference to Method A. Volume $V_0$ is calculated (step 510) from the equation above, plugging in the values for dP/dt and $f_0$. Finally, TGV, RV and TLC are calculated (step 512) as described above with reference to FIG. 11.

The flow rate $f_0$ is easily determined just prior to the shutter occlusion. However there are a few alternatives for finding the correct slope in the pressure (dP/dt) immediately following the closing of the shutter, without being affected by noise or other disturbances caused by shutter operation. Some of the options are as follows:

1. Measure the slope of the pressure curve (dP/dt) at the very beginning of the pressure rise following shutter occlusion;

2. Measure the slope (dP/dt) after an identifiable point on the pressure curve, which may represent the point of equating the pressure in the lungs to pressure at the mouth;

3. Ignore the first oscillation in the pressure curve and extrapolate backwards the main body of the pressure curve to the beginning of the pressure rise. This extrapolation results in the calculation of the pressure curve slope (dP/dt).

As shown in FIG. 15, the flow rate just prior to the shutting event is determined by the average of the flow rate over approximately 20 ms prior to the shutting event, depicted by line 300. This type of averaging is quite powerful, and even in cases of low flow rates, (around 0.2 L/sec, for example), when the noise may be as high as ±0.05 L/sec, averaging may take the uncertainty down by a factor of ~4.5, namely bring it to around ±5%, which is tolerable.

The slope of the pressure curve (dP/dt) is estimated by fitting a curved smooth function to the pressure curve along the first 30 ms starting at the "knee region". In this way the exact starting point, and any other specific point in this region, does not have a crucial effect on the final result. Hence, the result is relatively unaffected by the exact selection of the fitting range by the operator, or by the existence of the typical oscillation at the "knee region", as long as it is not too large.

As to the fit function, an exponential of the form $A-B\exp(-C \cdot t)$ (where A, B and C are the fit parameters) can be used. This function has been found by trial and error as a function that fits to the various shapes that the pressure curve presents in this region. The slope is calculated at the starting point of the curve (namely at t=0) as $B \cdot C$.

Variations to method B may include, for example, the fitting of any general smooth function to the pressure curve, and estimating the slope at any given point $t > t_0$. For example, the fit function may be of the form:

$$f = A - B \cdot \exp(-C \cdot t) + D \cdot t$$

As one example, the fit range may be changed from 30 ms to 50 ms, and the evaluation of the slope may be done at t=5 ms. The slope is thus given in this example by $$f = B \cdot C \cdot \exp(-C \cdot t) + D|_{t=5}$$

Another variation of Method B may be the fitting of a sinusoidal component to the oscillations, which could help difficulties in fitting a smooth function to the pressure curve when the oscillations on the pressure curve following the shutter closing are large. Thus, the fit function may be of the form $$f = A - B \cdot \exp(-C \cdot t) + D \cdot t + E \cdot \sin(F \cdot t + G)$$

The sinusoidal component then fits to the oscillations, and the smooth component emulates the net slope of the pressure curve. The slope of the smooth portion of the fit function at any point t may be again evaluated by $$f = B \cdot C \cdot \exp(-C \cdot t) + D|_t$$

Example Using Method B:

Referring again to FIG. 16, to calculate $V_0$ according to Method B we find $f_0$ to be $f_0 = 1.22$ L/sec. The slope of the interpolated smooth function, estimated 10 ms after the shutter closing (namely after point) to minimize the effects of the oscillations following the shutter closing, is 333 mmHg/sec. According to method B we thus find $$V_{0[B]} = \frac{P_0 F_0}{dP/dt} = 760 \frac{1.22}{333} = 2.78L$$

hence $$RV_{[B]} = V_{0[B]} - RV_{ADJ} = 2.78 - 0.81 = 1.97L$$

To summarize, the examples provided in Method A and Method B provide substantially the same result, which is also in agreement with the measured RV for this individual, which is approximately 2.0 L, measured by body plethysmography. Small differences between the results of the two methods as well as the difference with respect to results using body plethysmography are associated with measurement noise and may be reduced through averaging.

Example with Results

Table 1 below details typical results obtained from measurement of a human volunteer. During measurement, the volunteer would breathe normally through the device which was attached to his mouth through a mouthpiece, so as to ensure that there is absolutely no escape of air between the lips and the mouthpiece. A nose clip ensures there is no escape of air through the nose. While breathing, the volunteer holds his hands on his cheeks, to prevent sudden blowing of the cheeks when the shutter closes. The device recorded flow and pressure data continuously.

Each measurement consisted of a series of breathing cycles, while in each exhale portion the shutter was shut momentarily and opened again. In the last breathing cycle the volunteer was asked to exhale forcefully and fully, so that by the end of the last breathing cycle it is assumed the volume of the lungs reaches the volunteer's RV level. During the shutter event the flow signal drops abruptly to zero and the pressure rises sharply as the pressure in the lungs grows.

Table 1 presents results of six (6) measurements taken over a period of two weeks. The table compares RV results that were calculated using Method A (presented as $RV_{[A]}$) and RV results that were calculated using Method B (presented as $RV_{[B]}$). The average of all six measurements is compared to the body plethysmograph RV results of the same individual, obtained in accordance with ATS guidelines. VC results measured were in agreement with VC results calculated by a body plethysmograph, and thus, TLC results were in agreement with body plethysmograph's results as well.

TABLE 1

| | 1 | 2 | 3 | 4 | 5 | 6 | average | Body Plethysmograph |
|---|---|---|---|---|---|---|---|---|
| $RV_{[A]}$ | 2.46 | 2.35 | 2.29 | 2.28 | 2.29 | 2.48 | 2.36 | 2.39 |
| $RV_{[B]}$ | 2.17 | 2.41 | 2.43 | 2.15 | 2.20 | 2.45 | 2.30 | 2.39 |

The results shown in Table 1 above show that there is agreement between the results obtained by the industry standard (i.e., body plethysmograph), and the results obtained by the device and method of the present invention. These results show that the device and method of the present invention adequately measure a person's RV, TGV, and TLC.

Figure 17:
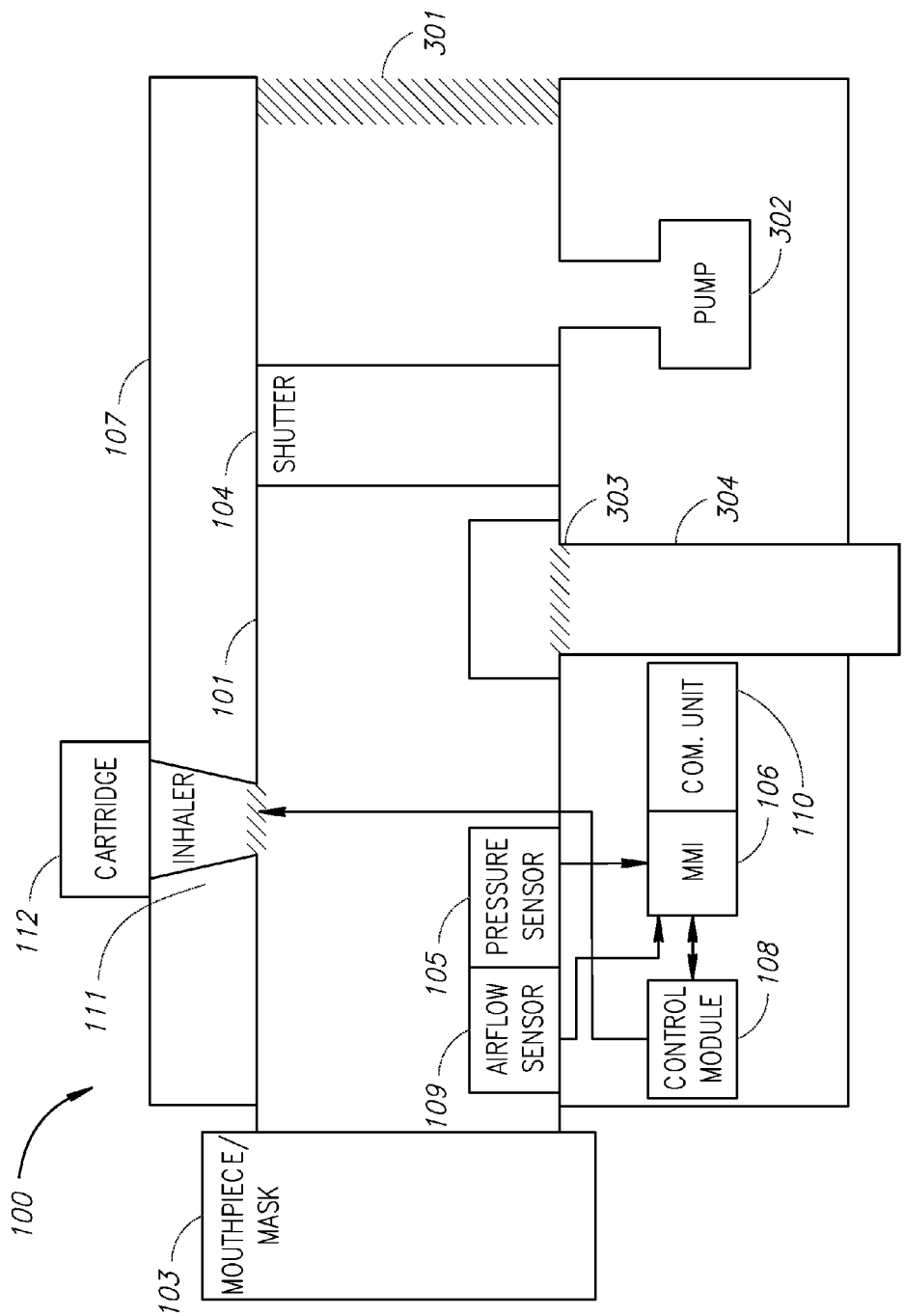
FIG. 17 is a schematic illustration of a breathing device for performing controlled injection or extraction of air into the occluded airways, according to some embodiments of the present invention.

FIG. 17 is a schematic illustration of a breathing device for performing controlled injection or extraction of air into the occluded airways. In some embodiments, the breathing device 100 may perform a rapid injection or extraction of air, also suitable for a Negative Expiratory Pressure (NEP) test, while measuring instantaneous alveolar pressure and/or volume. Breathing apparatus 100, in the illustrated embodiment, includes sensors 105 and 109, a Man-Machine Interface (MMI) 106, a communication unit 110, a shutter 104, a control module 108, and a mouthpiece/mask 103. Such components, may be substantially similar to corresponding components described in FIGS. 1-4 above.

The breathing apparatus 100 illustrated in FIG. 17 also includes a closable flow tube 304 having a valve 303 that is connected to the chamber 101 between the shutter 104 and the mouthpiece 103. The illustrated breathing apparatus 100 also includes a ventilation valve 301 that is positioned in the backend of the chamber 101, and a pump 302 that is connected to the chamber 101 between the shutter 104 and the ventilation valve 301. In some aspects, the pump 302 is designed to propel air away from the chamber 101, thereby to induce expiration or resist inspiration. Optionally, the pump 302 may be designed to propel air into the chamber 101, and thereby induce inspiration or resist expiration. In some aspects, the pump 302 may be designed to oscillate to periodically propel air in and out of the chamber 101. The period of oscillation may be predetermined and/or dynamically adjusted.

In some embodiments, the closable flow tube 304 may be a T shaped tube that allows the airflow in the breathing device 100 to bypass the shutter 104. Alternatively, the closable flow tube 304 may be a T shaped tube that directs airflow into a sealed container. The closable flow tube 304 may be closed automatically and/or manually at one or more velocities.

The pump 302, in some aspects, is located between the mouth of the user and the shutter 104. Alternatively, the shutter 104 is located between the mouth of the user and the pump 302. Optionally, the chamber 101 is connected to an external container of varying volumetric capacity. Optionally, the pump 302 injects or extracts air from the portion at a rate that is comparable to or significantly faster than the airflow rate of respiration at the instant of measurement.

As illustrated, shutter 104 is constructed in the chamber 101, for example in a plane that is perpendicular to an axis between the ventilation end 102 and the mouthpiece end 103. In such a manner, the shutter 104 may regulate the passage of air flux in the chamber 101. The shutter 104 is connected to a control module 108 that is designed to control the opening and/or closing of the shutter 104, for example as outlined above and described below. The control module 108 is optionally designed for receiving the outputs of the pressure sensor 105 and optionally a respiratory airflow sensor 109, for example as described below, and executing the exemplary methods herein. In some aspects, outputs of the control module 108 may be presented on the MMI 106. In some embodiments, the respiratory airflow sensor 109 and the pressure sensor 105 are the same sensor.

The pressure sensor 105, in the illustrated configuration of the breathing device 100, is positioned between the shutter 104 and the mouthpiece end 103. The pressure sensor 105 may be any pressure measurement component, such as manometer or sensor for the measurement of absolute pressure with an analog to digital sampling rate of 100 Hz, 1000 Hz, 5000 Hz, 10,000 Hz or any intermediate value or larger value. In some embodiments, the pressure sensor 105 may be a pressure sensor as described in Honeywell Catalog #40PC001B1A. Alternatively, the pressure sensor 105 may be a pressure sensor such as a Samba 3000 pressure transducer, which is available from Linton Instrumentation of Norfolk, England. Of course, these are examples, and other pressure measuring sensors may be used for the pressure sensor 105.

The pressure sensor 105 may be fabricated for example from a respiratory airflow resistive means and a differential pressure manometer, or alternatively from a Pitot tube and a differential pressure manometer. The differential pressure manometer may be any suitable sensor with an analog to digital sampling rate of 100 Hz, 1000 Hz, 5000 Hz, 10,000 Hz or any intermediate value or larger value. Such differential pressure manometers may be similar or identical to the differential pressure manometer described at Honeywell Catalog #DC002NDR4.

In some aspects, a flow sensor 109, such as a mass respiratory airflow sensor, is positioned in the chamber 101. In the illustrated embodiment, the flow sensor 109 is positioned between the shutter 104 and the mouthpiece end 103. The flow sensor 109 may be any flow sensor, such as a hot wire mass respiratory airflow sensor.

In the illustrated embodiment, the chamber 103 is constructed in a housing 107 generally sized and shaped so that it can be held comfortably in one hand and held-up to a user's mouth while measuring the pulmonary alveolar pressure of the user, for example as outlined above and described below. The device 100 may also be configured so that the user can comfortably hold the device and self monitor their respiratory parameters.

In some embodiments, the breathing device 100 includes the illustrated MMI 106. The MMI 106 may include a control panel, for example a keypad, a touch screen, and a set of buttons, and a liquid crystal display (LCD) screen. The keypad may include a start button, a selection button or other controls as desired to operate the breathing device 100, measuring pulmonary alveolar pressure of the user and or triggering shutter events. As illustrated, the MMI 106 may be communicably coupled to the control module 108 (which contains one or more processors or microprocessors for executing instructions stored on a tangible, computer readable media) to provide, for example, an interface for a user with the control module 108 and/or display results of processing performed by the control module 108. The control module 108 may be also be communicably coupled to a memory (not shown) to store the measured pressure, the calculations which are based thereon, and/or instructions for execution on the aforementioned processors.

In some embodiments, for example, the control module 108 may be any computer or processing device such as, for example, a blade server, general-purpose personal computer (PC), Macintosh, workstation, Unix-based computer, or any other suitable device. In other words, the present disclosure contemplates computers other than general purpose computers as well as computers without conventional operating systems. Control module 108 may be adapted to execute an operating system including Linux, UNIX, Windows Server, or any other suitable operating system. Further, the control module 108 may be communicably coupled to or include a local memory. The memory may include any memory or database module and may take the form of volatile or non-volatile memory including, without limitation, magnetic media, optical media, random access memory (RAM), read-only memory (ROM), removable media, or any other suitable local or remote memory component. The memory may include any data, software application, source code, objects, modules or other algorithms, as well as any other appropriate data such as VPN applications or services, firewall policies, a security or access log, print or other reporting files, HTML files or templates, data classes or object interfaces, child software applications or sub-systems, and others.

In a typical operation, the device 100 may be used for measuring a pulmonary alveolar pressure. For instance, pressure in the lungs is not uniform during normal respiration. A pressure gradient between the mouth and the lungs causes air to flow during normal respiration. During expiration, the airways' contraction and the elastic properties of the chest-wall, the diaphragm, and/or the alveoli may increase the pressure in the lungs above the pressure at the mouth ($P_m$), thereby inducing the expulsion of air from the lungs. During inspiration, inspiratory muscles cause the thoracic cage to lower the alveolar pressure below the pressure at the mouth, causing air to enter the lungs. As used herein, the term alveolar pressure ($P_{Al}$) means maximal and minimal pressure at the lungs during expiration and inspiration, respectively, at any given instant. In active lungs of a healthy user, for example during a continuous normal respiration, $P_{Al}$ means a maximal pressure in the alveoli during expiration and minimal pressure in the alveoli during inspiration. In static lungs of a healthy user, $P_{Al}=P_m$.

In some embodiments of the illustrated device 100, the shutter 104 and/or the chamber 101 may be adjusted to apply various resistance levels during an airway occlusion event. The difference between $P_m$ and $P_{Al}$ during breathing depends on the airway and device resistance. For example, the higher the airway and device resistance, the higher are $P_m$ and $P_{Al}$ amplitudes required to sustain a certain flow rate. In addition, for a given $P_{Al}$, $P_m$ increases and the flow rate decreases with the incrementing of the device resistance. As the device resistance is configurable, the occlusion events may be changed. Optionally, the device resistance is different for expiration and inspiration. Additional, in some embodiments, the device resistance may be dynamically changed (e.g., automatically by the control module 108). For example, the device resistance during a time interval prior to the occlusion event may be configured to be higher than the device resistance during an interval immediately after occlusion has ended. Such a configuration may aid in the reduction of Expiratory Flow Limitation prior to the occlusion event, thus reducing the time it takes alveolar and mouth pressure to equilibrate and improving the accuracy of the measured instantaneous volume. The variation of the resistances may be obtained by partially occluding airways by the shutter 104, for example, by changing a closure setting of the shutter 104 such that, at a particular setting, the shutter 104 partially occludes the airways in a closed state and, at another setting, the shutter 104 fully occludes the airways in the closed state). Optionally, the variation of the resistances may be obtained by allowing the user to manually change the caliber of the chamber 101 and/or the place of diffusive elements therein. Optionally, the variation of the resistances is obtained by allowing the user to use the MMI 106 for selecting a resistance.

In some aspects, the resistance may be varied for allowing one or more of the following. For instance, the resistance may be varied for endurance testing of the respiratory muscles via challenge breathing. The resistance may also be varied for challenge testing. The resistance may also be varied for peak $P_{Al}$ testing of muscle strength. The resistance may also be varied for training respiratory muscles. For instance, targeted inspiratory resistive or threshold inspiratory muscle training significantly improves inspiratory muscle strength and endurance. Thus, training respiratory muscles may decrease dyspnea for adults with stable COPD, see Geddes E L, Reid W D, Crowe J, O'Brien K, Brooks D. Inspiratory muscle training in adults with chronic obstructive pulmonary disease: a systematic review. Respir Med. 2005 November; 99(11):1440-58. The resistance may also be varied for the calculation of a respiratory system compliance index. For example, when resistance is relatively high during relaxed expiration, resulting in a slow expulsion of air, the elastic force of contraction of the respiratory system is in quasi-equilibrium with the airway resistive force. Thus, $P_m$ approximately equals $P_{Al}$ and a respiratory system compliance index can be calculated using $$C = \frac{V_a - V_b}{P_{Al}}$$

where $V_a$ denotes lung volume at the instant of measurement and $V_b$ denotes a lung volume level at which alveolar pressure is zero, for example FRC level or zero volume.

Figure 18A:
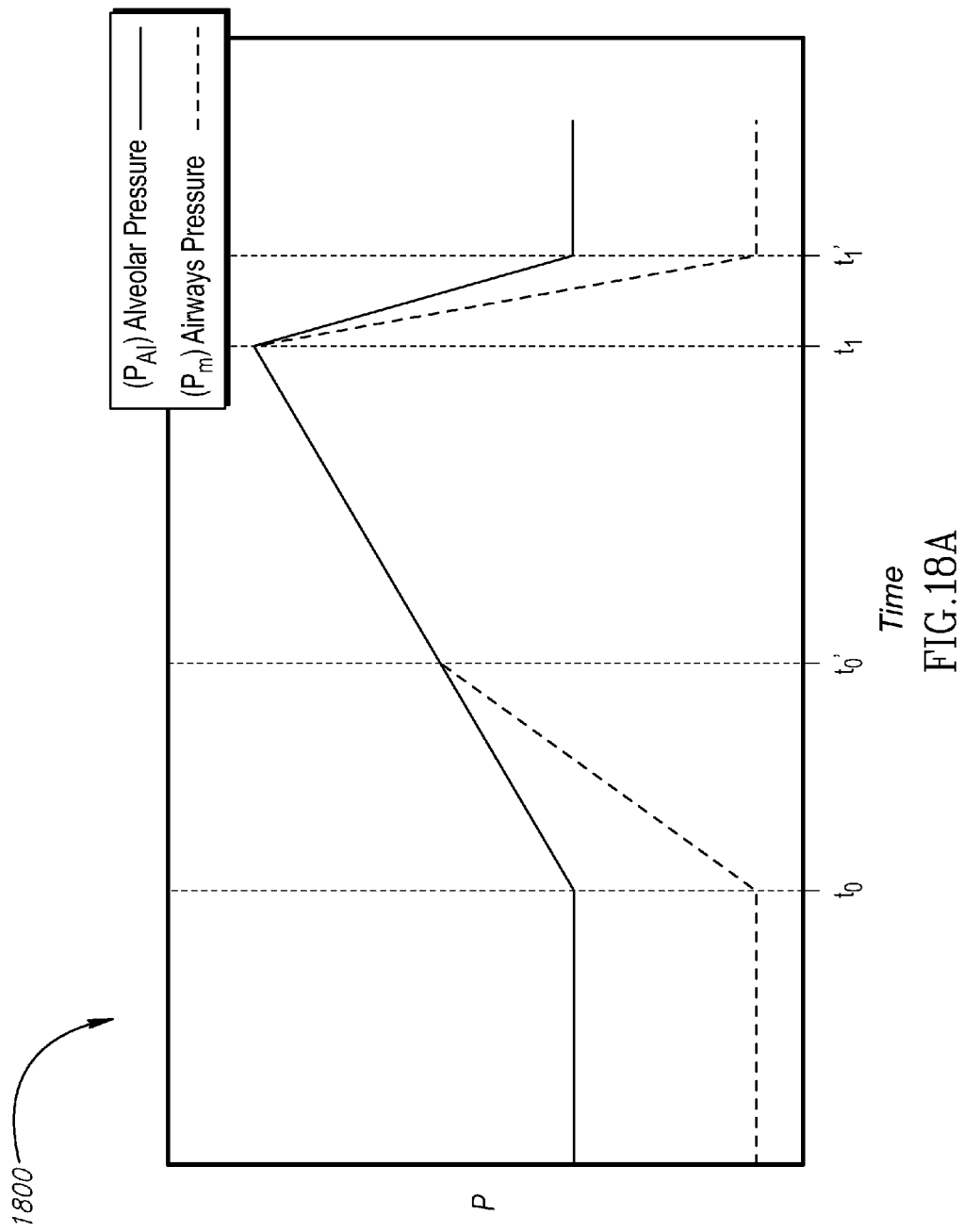
FIG. 18A is a graph that schematically depicts the time dependence of alveolar and airway pressure in lungs in reference to the instants described in FIG. 18B, according to some embodiments of the present invention.
Figure 18B:
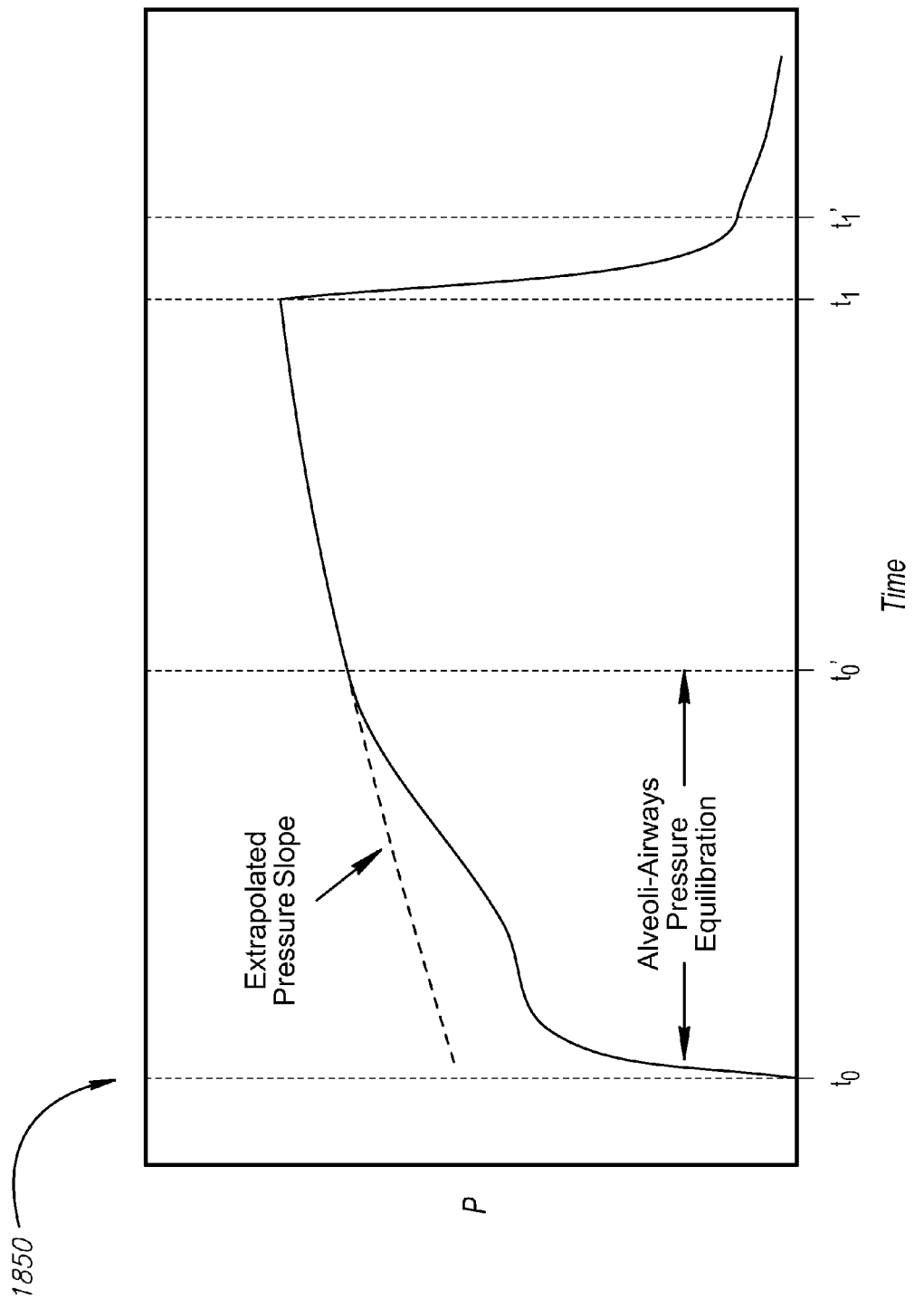
FIG. 18B is a graph depicting time dependence of air pressure at the airway during an airway occlusion event, and an extrapolated alveolar pressure line, according to some embodiments of the present invention.

Turning to FIG. 18A, this figure illustrates a graph 1800 that schematically depicts a time dependence of alveolar and airway pressure in lungs in reference to the instants described in FIG. 18B. FIG. 18B illustrates a graph 1850 depicting time dependence of air pressure at the airway during an airway occlusion event (e.g., an interruption) and an extrapolated alveolar pressure line. During such interruption, $P_{Al}$ and $P_m$ are equilibrated. Optionally, the interruption is made in a normal respiration cycle while the user is continuously breathing. For clarity, as used herein a respiration cycle means one or more circulatory exhalations and inhalations. For example, a respiration cycle starts at substantially full tidal exhalation and stops at substantially full tidal inhalation. Optionally, the respiration cycle includes a respiration hold introduced before, during, and/or after the exhalation and/or inhalation. The respiration cycle may be a natural respiration cycle as well as an artificial respiration cycle. The respiration cycle may be a tidal breathing respiration cycle, an exertion tidal breathing respiration cycle, and/or guided respiration cycle.

Optionally, the equilibrium is achieved by occluding the airways of the user, optionally externally, and the occlusion of airways is achieved within a period of less than 25 milliseconds (ms), and preferably within less than 10 ms. For clarity, the occlusion may be at zero flow conditions, an expiratory and/or an inspiratory occlusion of the airways at various levels of respiration rates, such as at resting and exertion. Optionally, when the lungs are fully relaxed, resulting in negligible flow at the mouth and negligible $P_{Al}$, occlusion of airways may be achieved within a period longer than 25 ms.

In use, the user breaths spontaneously via the breathing end 103 of device 100 in FIG. 17, an endrotracheal tube, or a mask that is connected thereto. In such a manner, the user's respiratory inhalation and exhalation cycles are performed via the chamber 101. The control module 108 instructs the activation of the shutter 104 or the instruction to activate the shutter 104 is provided manually by the user or a technician to perform an airway occlusion event during one or more of the normal respiratory cycles of the user. In each airway occlusion event, the shutter 104 is substantially occluded within less than 25 ms, optionally less than 15 ms, preferably less than 10 ms, for example 6 ms, 2 ms, 1 ms, and 0.5 ms, and then instantaneously reopened after a duration that may vary between 40 ms to several seconds. The transition from an occluded state to a substantially open state of the airways is achieved within less than 15 ms, optionally less than 10 ms, and preferably less than 6 ms, for example 5 ms, 4 ms, 2 ms, 1 ms.

The instruction to reopen the shutter 104 is provided automatically by the control module 108, or manually by a technician or the user. The occlusion duration may be fixed, manually determined or particular to each occlusion event based on the rate of change of the airway pressure during the occlusion. As used herein a substantial occlusion is an occlusion of at least 75% of the airway, for example 75%, 80%, 85%, 90%, 95%, 100% or any intermediate value. As used herein a substantially open state of the airways is an opening of at least 75% of the airway, for example 75%, 80%, 85%, 90%, 95%, 100% or any intermediate value.

Optionally, the shutter 104 is designed to have a minimal effect on the response of the lungs to the occlusion, for example by inducing a minimal amount of mechanical work thereon. Optionally, the occlusion is imperceptive to the user undergoing the measurement so as to assure that no respiratory change that might affect the normal $P_{Al}$ is aroused by the occlusion shutter action.

In some embodiments, the pressure waves produced by the occlusion mechanism (e.g., shutter 104) are calculated and subtracted from the pressure signal of the lungs. In such a manner, a shutter 104 that generates less moderated occlusion pressure waves may be used without compromising the quality of the pressure signal of the lungs. For example, as outlined above, the opening and/or occluding of the shutter 104 may involve the movement of surfaces that perform work on the lung. The work done on the lungs may be approximated by invoking the first law of thermodynamics as follows:

$$dW = \int_{t_0}^{t_0 + \Delta_{Occlusion}} P \hat{f} dt$$

where dW denotes work; $\hat{f}$ denotes a flow rate change produced by the occlusion or opening of the shutter, for example by the motion of surfaces perpendicular to the flow; P denotes pressure; t denotes time; and $\Delta_{Occlusion}$ denotes the interval between the instant at which the shutter begins to close and the instant of full occlusion (and vice versa). The amount of work that is applied on the lungs may be used for determining its contribution to changes in $P_{Al}$ at $t_0 + \Delta_{Occlusion}$. This contribution may be neutralized or reduced for improving the accuracy of the calculation of $P_{Al}$ at $t_0$ or close to it.

In some embodiments of the present invention, the movement of one or more of the user's cheeks is limited for decreasing the responsiveness thereof to the airway occlusion events. Optionally, the limitation is performed by manually holding the cheeks, for example by instructing the user to hold her cheeks, by a caretaker, and/or automatically by a designated mask that is connected to the breathing device 100.

Figure 19:
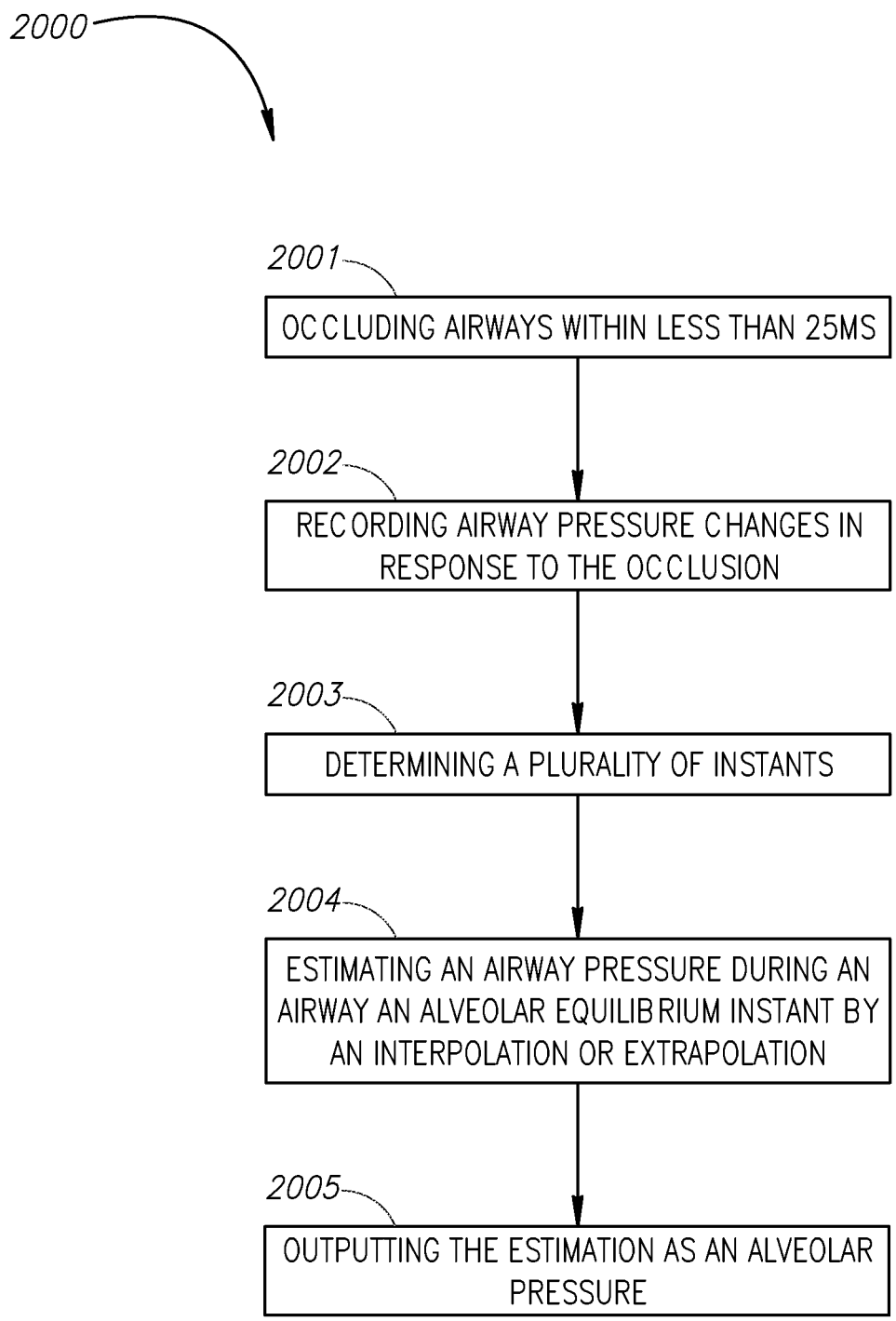
FIG. 19 is a flowchart of a method for measuring pulmonary alveolar pressure, according to some embodiments of the present invention.

FIG. 19 is a flowchart of a method 2000 for measuring pulmonary alveolar pressure $P_{Al}$, according to some embodiments of the present disclosure. First, as shown at 2001, a respiratory airflow of a user breathing via a breathing device, such as the breathing device 100, is interrupted. During such interruption, which may be referred to herein as an airway occlusion event, $P_{Al}$ and $P_m$ are equilibrated. The interruption may occur through a variety of techniques. For example, the interruption is made in a normal respiration cycle while the user is continuously breathing. The equilibrium may be achieved by occluding the airways of the user, for example, externally. In the illustrated step 2001 of method 2000, the occlusion of airways is achieved within a period of less than 25 ms, and preferably within less than 10 ms. The occlusion may be an expiratory and/or an inspiratory occlusion of the airways at various levels of respiration rates, such as at resting and exertion.

In step 2002, airway pressure changes are recorded in response to the occlusion. For instance, turning briefly to FIG. 18B, this figure illustrates airways air pressure during the airway occlusion event in device 100 and lungs that efficiently suppress high frequency (i.e., frequencies above 100 Hz) pressure waves, at the instants also depicted in FIG. 18A. For clarity, P denotes the intrathoracic pressure; t denotes time; $t_0$ denotes an interruption initiation instant, such as an airway occlusion initiation instant during which the shutter 104 begins to occlude; $t_0'$ denotes the instant of equilibrium between $P_{Al}$ and $P_m$; $t_1$ denotes an interruption termination instant, such as an airway occlusion reopening instant at which the shutter reopens; and $t_1'$ denotes a pressure release instant, such as an instant during which the intrathoracic pressure gradient is substantially equal to the pressure gradient at $t_0$ for the first time after $t_1$.

As shown in FIG. 18A, a pressure gradient exists between the mouth and alveoli during a normal respiration cycle. At $t_0$, the user's airways are occluded and $P_m$ rises or decreases until the pressure between the airways and alveoli equilibrates at $t_0'$. From thereon the intrathoracic pressure changes uniformly, in accordance with Boyle's law. At $t_1$, the shutter reopens and the pressure gradient between $P_m$ and $P_{Al}$ is restored.

Returning to FIG. 19, a plurality of instants are determined at 2003. For instance, as shown at FIG. 18B, a plurality of instants and the airway and alveolar equilibrium instant are determined during the airway occlusion event by analyzing the recorded actual pressure and the recorded actual flow rate. Optionally, the plurality of instants are $t_0$, $t_1$, and $t_1'$. The instants $t_0$, $t_1$, and $t_1'$ may be identified by correlating the instants $t_0$, $t_1$, and $t_1'$ with extrema points of a smoothed second derivative of the pressure recorded shortly prior to, during, and after the occlusion event.

Returning to FIG. 19, an airway pressure is estimated during an airway and alveolar equilibrium instant at 2004. The estimation may be done through, for example, interpolation or extrapolation. As shown at FIG. 18B, for instance, the airway pressure during one or more other intermediate instants, such as the airway and alveolar equilibrium instant $t_0'$, are estimated, by an interpolation or extrapolation of the recorded actual pressure at the plurality of known instants, such as $t_0$, $t_1$, and $t_1'$. Alternatively, or additionally, a smoothed pressure curve from $t_1$, or any earlier point at which pressure interferences are not significant toward $t_0'$ and/or before, such as for example, towards $t_0$, is generated according to the interpolation or extrapolation. In some aspects, the interpolation or extrapolation is based on a spline interpolation, an exponential interpolation, and/or a polynomial interpolation.

In use, the pressure at the equilibrium instant $t_0'$ is calculated from the smoothed pressure curve. The pressure at $t_0'$ represents the pressure at $P_m$ when $P_m = P_{Al}$. As such, the pressure at $t_0'$ is indicative of $P_{Al}$ at $t_0'$.

Optionally, the alveolar pressure at $t_0$ (i.e., the alveolar pressure just prior to the interruption) is substantially different from the alveolar pressure at $t_0'$. In such instances, the alveolar pressure at $t_0$ may be calculated in order to determine respiratory parameters of the user. Now, the pressure slope between $t_0'$ and $t_1$ is the slope of the alveolar pressure while prior to $t_0'$ (i.e., between $t_0$ and $t_0'$) the pressure slope does not truly record alveolar pressure. Therefore, alveolar pressure at instants prior to $t_0'$ may be calculated by back extrapolation of the pressure slope between $t_0'$ and $t_1$, or $t_0'$ and some other intermediate instant between $t_0'$ and $t_1$. In some aspects, the pressure slope may be backwards extrapolated to the instant $t_0$ where $P_{Al}$ at $t_0$ is determined.

It should be noted that backwards extrapolated pressure slope that is based on data points of the pressure slope that include instances before $t_0'$ (i.e., between $t_0$ and $t_0'$) may result in an erroneous approximation of alveolar pressure. It may therefore be desirable to determine $t_0'$ before backwards extrapolating the pressure slope. Optionally the instant $t_0'$ may be determined by the existence of a change of trend in the pressure slope. Alternatively, the instant $t_0'$ may be set to be a constant interval during which alveolar and airway pressure are known to fully equilibrate. In some aspects, the backwards-extrapolated pressure slope is a linear, polynomial, spline, exponential or other backwards extrapolation that incorporates the first, second, third or above rate of change of the pressure with respect to time.

In some cases, airway occlusion events may result in pressure waves that affect the pressure reading at the chamber 101. Such waves may affect the reading of the pressure sensor 105 after the shutter closes. As such, pressure waves caused by the occlusion may reduce the accuracy of the reading of the pressure sensor during $t_0'$. Thus, in some aspects, $t_0'$ may be determined as the instant at which pressure interferences on the pressure slope become negligible.

Figure 20:
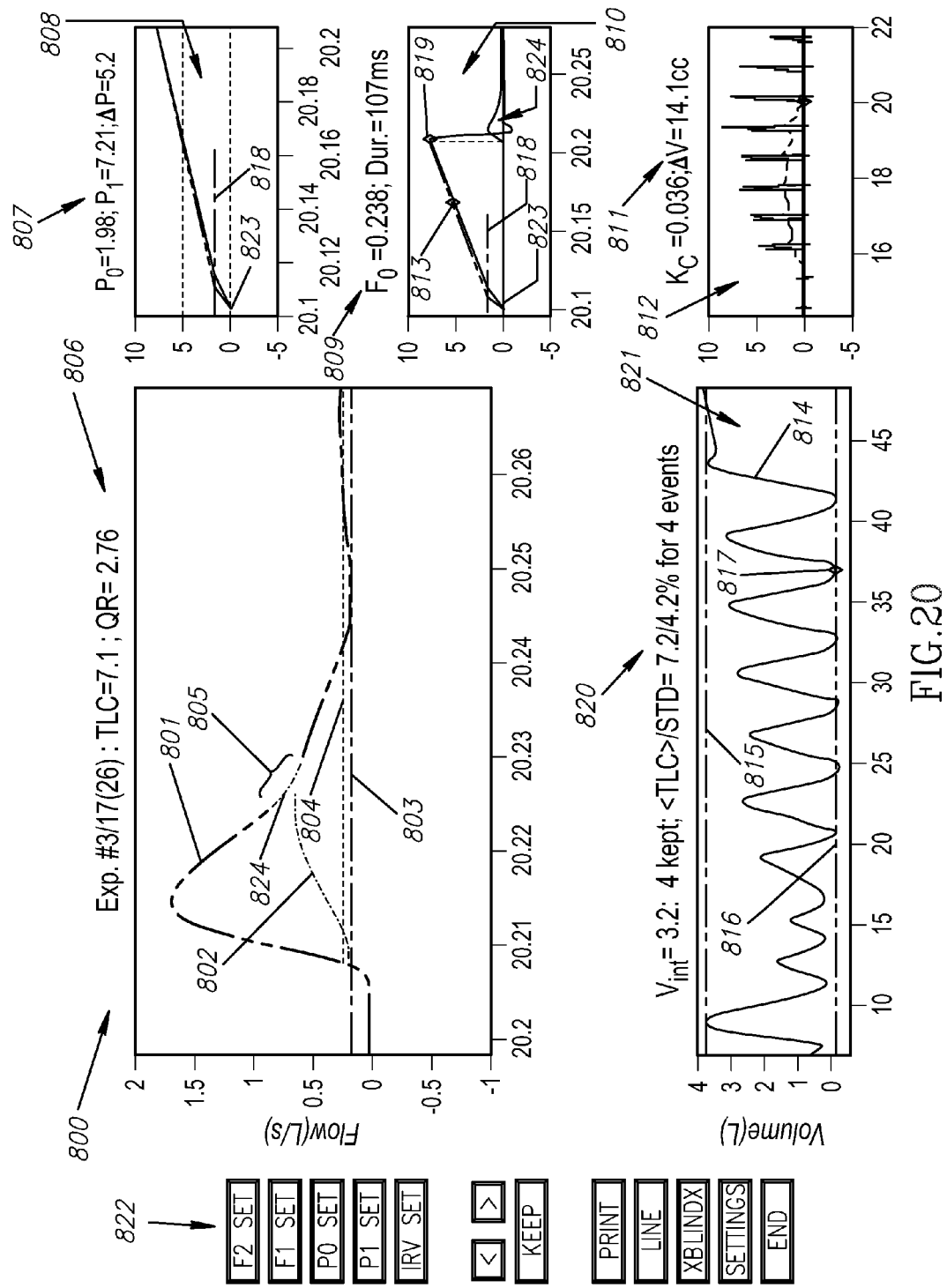
FIG. 20 is a screen shot of a user interface depicting parameters and graphs of variables relevant for lung volume measurement, according to some embodiments of the present invention.

After estimation of the air pressure during the airway and alveolar equilibrium instant is complete, this estimate may be taken (e.g., output to a user through, for instance, the MMI 106) as an Alveolar pressure, at step 2005. For instance, with reference to FIG. 20, this figure illustrates one embodiment of a graphical user interface (GUI) 800 depicting parameters and graphs of variables relevant for lung volume measurement, including graphs of the dependence of airway pressure, flow, and lung volume changes over time. Shown in 808 and 810 are the interpolated pressure curve, superimposed on the actual pressure reading during an occlusion event. The airway pressure at the instant of interruption is obtained by determining an instant $t_0'$ denoted by 813 between $t_0$, denoted by 823, and $t_1$, denoted by 819, at which equilibration between the $P_m$ and $P_{Al}$ may be assumed. The instant 813 may be chosen automatically as for example, the midpoint between $t_1$ and $t_0$; manually by the technician using the user interface tools 822; or by the slope of the airway pressure, as for example by requiring that the pressure curve be sufficiently close to a linear curve. As shown in 808 and 810, the actual pressure at $t_0$ is not equal to the backwards extrapolated pressure level, 818, at $t_0$.

As described above, in severely obstructed patients, $t_0'$ may occur significantly after $t_0$. Therefore, intrathoracic pressure changes due to volume changes that occur prior to $t_0'$ are not observed at the mouth. Thus, the backwards extrapolated pressure at $t_0$ or shortly after $t_0$ is the correct pressure to use for purposes of lung volume calculation, allowing the calculation of Alveolar pressure and related parameters, such as instantaneous lung volume, even in severely obstructed patients.

Alternatively, interpolated pressures at particular times may be output and displayed. For example, the interpolated pressure at $t_0'$, which is substantially equal to the actual $P_{Al}$, may be displayed. Optionally, the interpolated pressure at an instant between $t_0'$, and $t_0$ may be displayed.

In some embodiments, the process depicted in FIG. 19 may be repeated a plurality of times, for example 2, 5, 10, or any intermediate or larger number for improving the statistical validity of $P_{Al}$ and of the calculated TLC or RV and reducing the standard deviation of the averaged result. For example, as seen in 820 and 806, the occlusion event presented is a single event denoted as a third of 26 events ("#3/17(26)"), from which 17 were automatically selected to qualify for volume analysis. Out of the 17 events qualifying for analysis, 4 events have been manually or automatically accepted ("kept"). The 4 kept events yield an averaged TLC of 7.2 L with a standard deviation of 4.2%. The technician is thus informed by the MMI 106 of the statistical accuracy of the averaged calculated lung volume. Also appearing in 806 is a Quality Rating (QR) of the occlusion event, assisting the technician in evaluating the accuracy of the result or allowing for an automatic evaluation of the quality of the averaged lung volume. The outputted lung property, for example TLC, may thus be outputted with a Quality Rating, further supporting a diagnosis based on the outputted result.

The outputted pressure and lung volume may be presented using the aforementioned MMI 106 and/or forwarded to a computing unit via a communication unit that establishes a communication connection therewith, such an RS-232 connection, an Ethernet connection, a Wi-Fi™ connection, a WiMax™ connection, a universal serial bus (USB) connection, a Firewire™ connection, an USB2 connection, a Bluetooth® connection and an IR connection. The outputted pressure may be stored in a local memory unit or on a memory card. Optionally, the breathing device 100 comprises a memory card drive for allowing such storage. The memory card drive may be a CompactFlash™ card drive, a SmartMedia™ card drive, a Memory Stick™ card drive, a Secure Digital™ card drive, a miniSD™ card drive, and/or a MicroSD™ card drive, or any other Flash drive.

Figure 21:
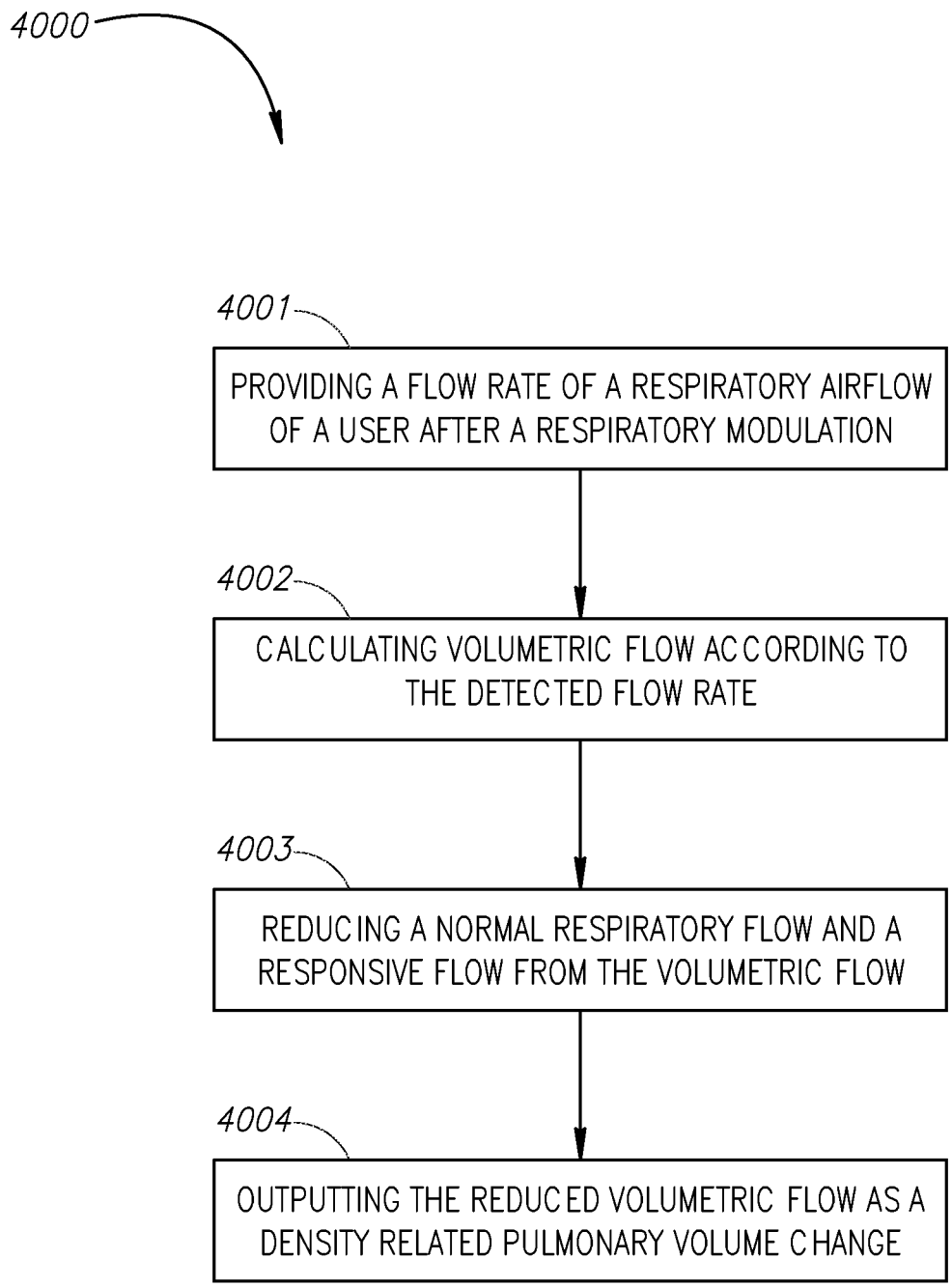
FIG. 21 is a flowchart of a method for measuring a density related pulmonary volume change which results from externally occluding the user's airway, according to some embodiments of the present invention.

FIG. 21 is a flowchart of a method 4000 for measuring a density related pulmonary volume change which results from externally occluding (e.g., respiratory modulation) the user's airway. The external occlusion, or, in some aspects, a respiratory modulation, may include an interruption, such as airway occlusion (e.g., an external airway occlusion) for a period of 40 ms and up to several seconds. Alternatively, any other respiration modulation or interruption, triggered and/or uninitiated, voluntary and/or non voluntary may produce the occlusion. Such a density related pulmonary volume change measurement may be used for evaluating the functioning of the lungs. For example, the method 400 may be used for detecting Expiratory Flow Limitation (EFL) during spontaneous quiet breathing, see Hage R., J. G. J. V. Aerts, A. F. M. Verbraak, B. van den Berg, and J. M. Bogaard: Detection of flow limitation during tidal breathing by the interrupter technique. Eur. Respir. J. 8, 1910-1914, 1995, which is incorporated herein by reference and forced breathing, see Ohya N, Huang J, Fukunaga T, Toga H., Mouth pressure curve on abrupt interruption of airflow during forced expiration. J. Appl. Physiol. 66: 509-517, 1989, which is incorporated herein by reference and other parameters described in International Application No. PCT/IL2010/00070, incorporated herein by reference. As such, the method 4000 may be used for diagnosing dyspnea, for example in chronic obstructive pulmonary disease (COPD) patients.

Thermodynamic processes in the lungs may be approximated using Boyle's law that states that the product of the pressure and volume of a fixed number of gas molecules at constant temperature is constant. Boyle's law may be written as follows:

$$V_0 = (P_0 + \Delta P)\frac{\Delta V}{\Delta P}$$

where $V_0$ and $P_0$ denote an initial pulmonary volume and pulmonary pressure and $\Delta V$ and $\Delta P$ denote variations in the pulmonary volume and the pulmonary pressure from the initial states. When interrupting the airways of the lungs, for example by occluding an airway of a user during normal respiration, the number of air molecules that remain in the occluded lung may be assumed to be fixed. $P_0$ and $\Delta P$ are optionally calculated by using the breathing device 100, for example as described above and in FIG. 18. $V_0$, which is optionally marked as the instantaneous lung volume at the airway occlusion event, may be obtained by calculating the contracted or expanded pulmonary volume $\Delta V$ as described above.

A flow rate of a respiratory airflow of a user after a respiratory modulation is provided in 4001. The respiratory modulation may be applied by a breathing device, such as the breathing device 100 depicted in FIG. 17. In another example, the respiratory modulation is made by applying instantaneous external pressure on the lung and/or on a portion of the user airway. In another example, the respiratory modulation is involuntary, such as a cough or any other act of exhaling air.

Optionally, the pressure in the airways of the user, denoted as $P_m$, is recorded during the respiratory modulation, for example using the breathing device 100, as described above. The airway occlusion event may also be performed, for example, as described above in relation to 2001 of FIG. 19.

The respiratory modulation initiation and termination, for example the occlusion initiation instant $t_0$ and the occlusion reopening instant $t_1$, are determined, such as according to step 2003 of method 2000.

Figure 22:
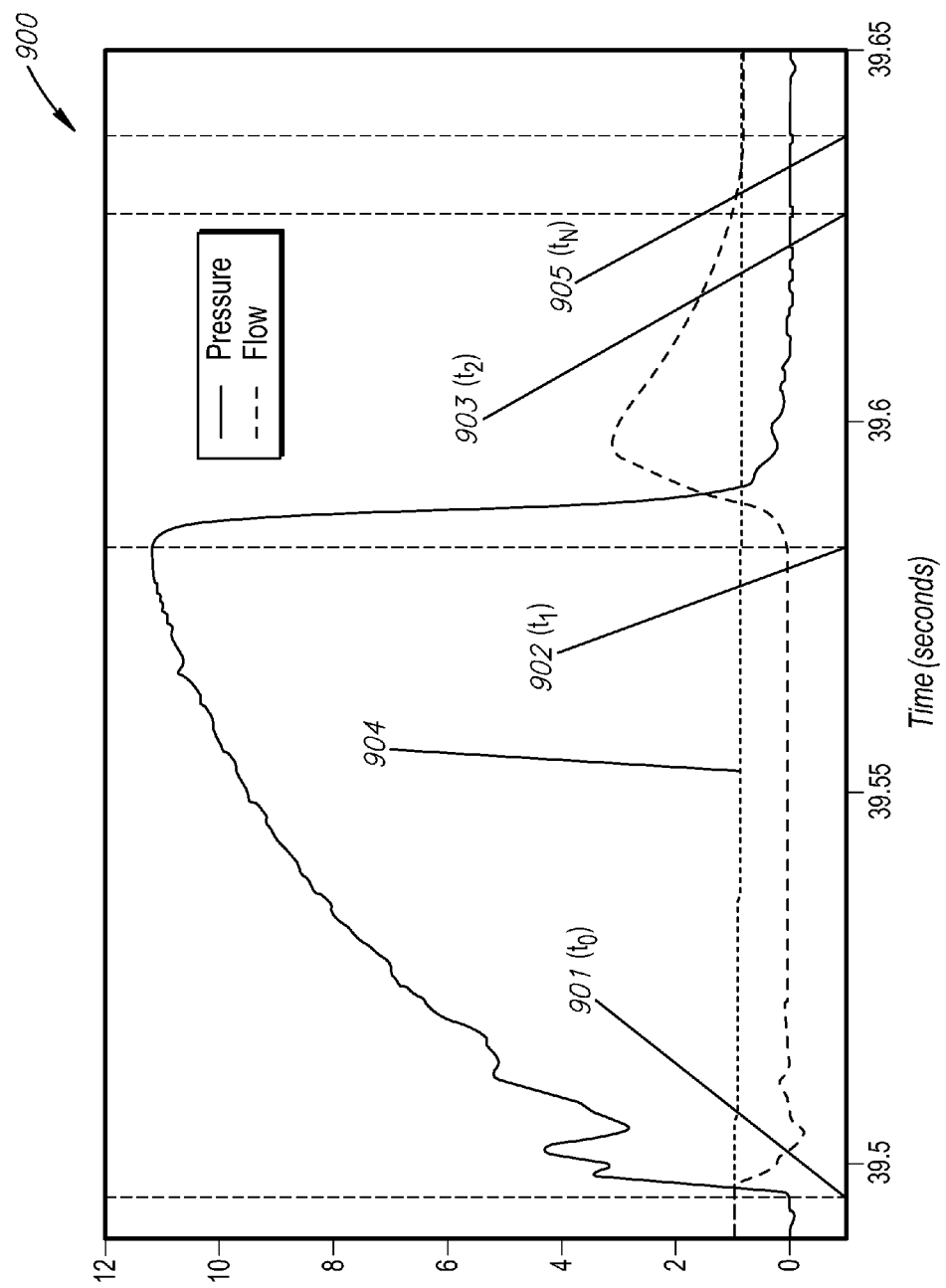
FIG. 22 is a graph of an exemplary flow rate curve as a dashed line, an exemplary airflow pressure curve as a solid line and an interpolated normal lung flow rate curve as a dotted line shortly prior to, during and after an airflow interruption event, according to some embodiments of the present invention.

Turning briefly to FIG. 22, $t_0$ and $t_1$ are denoted by the numerals 901 and 902, respectively, on the solid line curve in the graph 900. It should be noted that $t_0$ and $t_1$ may be calculated as described above, or by any other method that is based on an airway occlusion. FIG. 22 depicts a dashed line curve of the recorded flow rate in Liters per second (L/s) and a solid line curve of the airflow pressure in Torr units during the airway occlusion event. A dotted line curve of the normal lung volume rate of change 904 may be approximated by using the recorded flow rate before $t_0$ and after $t_1$ to interpolate the flow between $t_0$ and $t_N$ (905) as described below. Optionally, the interpolation is based on a spline interpolation, an exponential interpolation and/or a polynomial interpolation. It should be noted that the flow rate is assumed to be measured without interferences, such as leakage of air in or out of chamber 101.

Optionally, the flow rate after the respiratory modulation is detected and recorded using an airflow sensor in a breathing device, such as the sensor 109 in breathing device 100 in FIG. 17. In some aspects, the flow rate in the airway of the user, for example in the mouth, denoted as f, is recorded immediately after the airway occlusion event. The flow rate and the pressure may also be respectively determined according to the outputs of the respiratory airflow sensor 109 and the pressure sensor 105.

Figure 23:
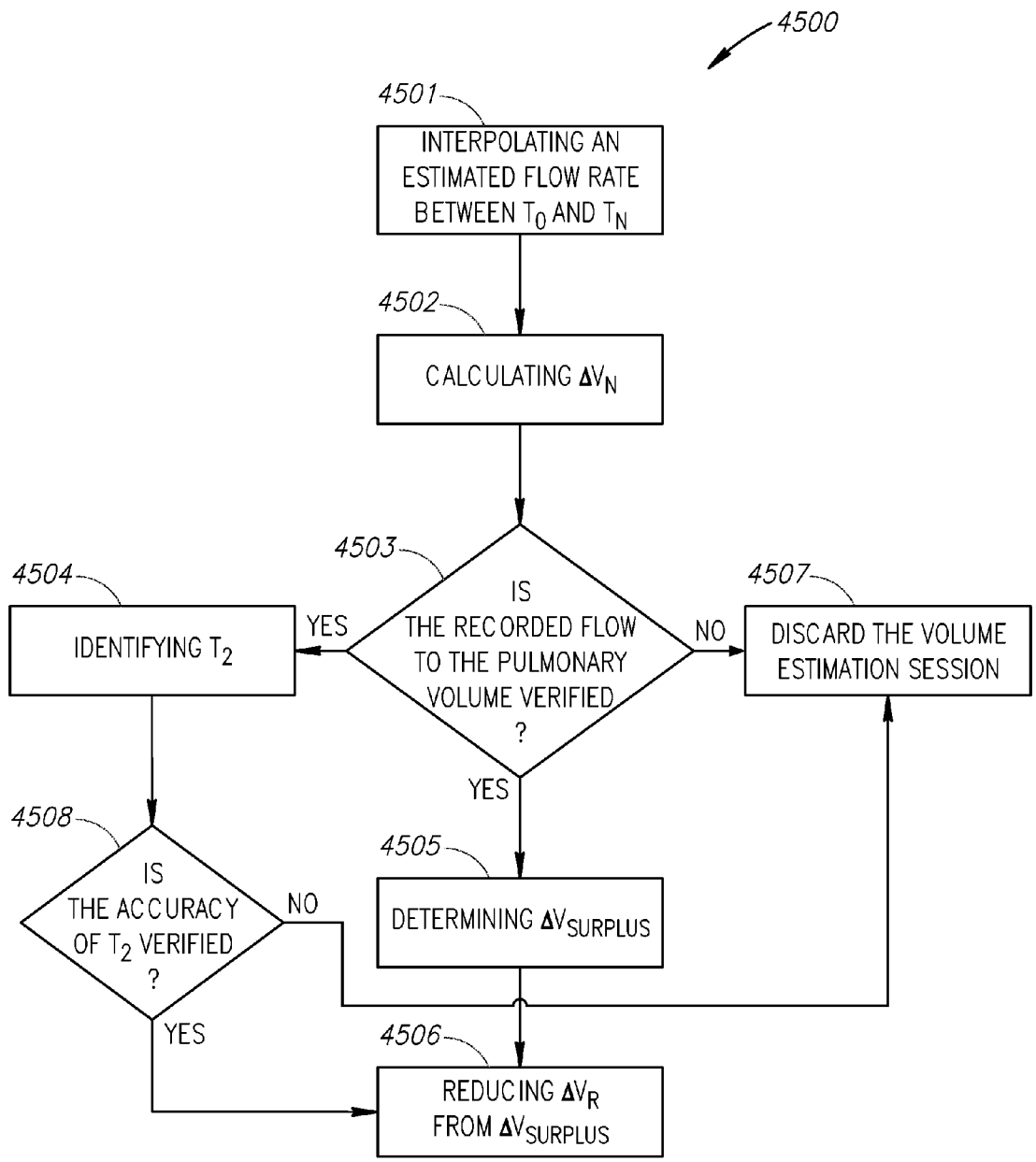
FIG. 23 is a flowchart of a process for reducing normal respiratory motion and responsive flows from the recorded flow rate data, according to some embodiments of the present invention.

The flow rate that is recorded after a respiratory modulation, such as the airway occlusion event, reflects flow rate changes which are affected by the occlusion and reopening of the airways. During the changes, the average lung pressure increases or decreases in relation to a pre-occlusion pressure prior to the respiratory modulation incurred by the occlusion. These pressure and flow rate changes are led by various processes, such as by the aforementioned respiratory modulation that is applied in the lungs, elastic forces, muscle work, inertia and the medical condition of the user. After the shutter reopens, the lungs return to their normal motion. An example of flow rate data during and after an airway occlusion event, from the beginning of the airway occlusion event until after the completion of the shutter reopening event, is shown on FIG. 17. An example of flow rate data after an airway occlusion event, from the beginning of the reopening of the airway occlusion until after the flow resumes its normal rate is shown in FIG. 23 and with reference to line 801 of FIG. 20.

The recording may allow estimating of an instant of normal flow, referred to herein as a normal flow instant and denoted as $t_N$. During the normal flow instant, the flow rate is a normal respiratory flow, for example a flow rate of air in a normal unoccluded airway, such as the flow rate before $t_0$. Optionally, in order to determine $t_N$, an instant and/or an average and/or a mean of the flow rate before $t_0$ may be recorded.

Figure 24:
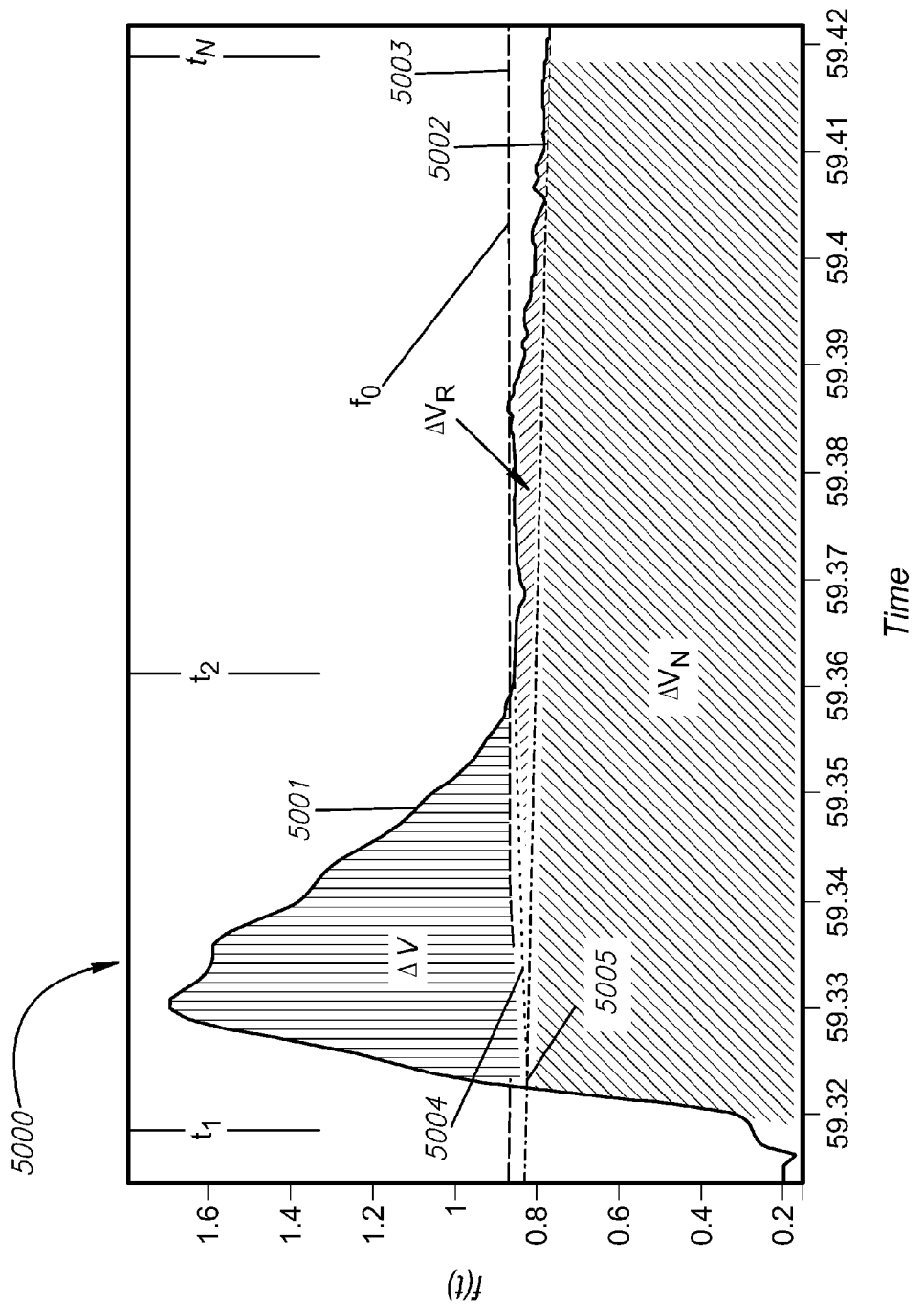
FIG. 24 is a graph of an exemplary flow rate curve and an exemplary interpolated flow rate curve after an airflow interruption, according to some embodiments of the present invention.

Alternatively, in order to determine $t_N$, an instant, an average and/or a mean of the flow rate after $t_1$ is recorded. In such embodiments, the recording is performed for a predefined period determined manually or automatically, for example, based on the properties of the airflow pressure curve after the respiratory modulation is performed. The recording may last for 2 minutes, 1 minute, 30 seconds, 20 seconds, 1 second, 0.5 second, 0.1 second, 10 ms or any intermediate value. For example, as shown in FIG. 24, the interval between $t_1$ and $t_N$ is about 105 ms and in FIG. 22, this interval is approximately 60 ms.

Optionally, the data is recorded while the intra-thoracic pressure is recorded as described in FIG. 18 above. The recorded data may be used as a reference value for determining the normal respiratory flow, for example, by correlating changes in the pressure slope with changes in airflow rate.

As shown at FIG. 21, at 4002, a volumetric flow that is induced by the respiratory modulation change is determined. For example, the volumetric flow may be determined by calculating an integral of the airway flow rate between the occlusion termination instant $t_1$ and the normal flow instant $t_N$ that is subsequent thereto. For clarity, $\Delta V_{Event}$ denotes an integral which may be calculated as follows:

$$\Delta V_{Event} = \int_{t_1}^{t_N} f\, dt.$$

As $t_N$ and $t_1$ are either known in advance or accurately calculated from the recorded data, $\Delta V_{Event}$ may be accurately calculated from the recorded flow rate data.

At 4003, a normal respiratory flow that is contributed by a normal respiratory motion and a responsive flow contributed by the aforementioned respiratory modulation, for example as an outcome of a compression wave, is reduced from the integral. At 4004, the reduced volumetric flow, which is optionally the density related pulmonary volume change, $\Delta V$, is output to, for example, the MMI 106.

The method depicted in FIG. 21 may be used for the assessment of EFL, for example, as described in Ohya N., Huang J., Fukunaga T., Toga H. Mouth Pressure curve on abrupt interruption of airflow during forced expiration. J. Appl. Physiol. 1989; 66: 509-517 which is incorporated herein by reference, and for the calculation of instantaneous lung volume by associating the calculated density related volume change $\Delta V$ with $\Delta V$ in Boyle's law, as described above, for other diagnoses, as in other types of diseases causing chronic airflow obstruction.

FIG. 23 is a flowchart of a process 4500 for reducing normal respiratory motion and responsive flows from the recorded flow rate data. Further, reference is made to FIG. 24, which is a graph 5000 of an exemplary flow rate curve f and an interpolated flow rate curve $f_N$, which is optionally calculated as described below, following the reopening of a shutter and an instant during which the flow rate returns to its normal state. For clarity, the recorded flow, f, is depicted as a solid line 5001, and an interpolation of at least a portion of the measured flow, $f_N$, is depicted in a dashed line 5002. The variables f and $f_N$ are shown between time instants $t_1$ and $t_N$. The illustrated flow rate curve f reflects the sum of the density related pulmonary volume change, ($\Delta V$), the normal respiratory flow contributed by a normal respiratory motion ($\Delta V_N$), and the responsive flow contribution of the respiratory modulation to the lungs responsiveness ($\Delta V_R$), (e.g., muscle and compliant responsiveness to the airway occlusion event). In addition, an $f_0$ baseline 5003 (also illustrated in FIG. 20 as 804), is shown for reference. Further, a line $f_S$ (illustrated in FIG. 20 as 802) connects the points $f(t_{1,N})$ (where $t_{1,N}$ denotes that instant when the recorded flow after $t_1$ equals the interpolated flow) and $f(t_2)$, as shown at 5004, for distinguishing between $\Delta V$ and $\Delta V_R$ above $f_N$.

First, as shown at 4501, an estimated flow rate between $t_1$ and $t_N$, denoted herein as $f_N$, is calculated according to interpolation. The interpolation is optionally based on a flow rate measured before $t_0$ and after $t_N$, as shown by the dashed line in FIG. 24, marked with numeral 5002, and in FIG. 20, marked as 803.

At 4502, $\Delta V_N$, may be determined by calculating the integral of the interpolated flow rate as follows:

$$\Delta V_N = \int_{t_1}^{t_N} f_N dt$$

As shown at 4503, the calculation of $\Delta V_N$ allows the performance of a verification calculation to assure that expression of one or more event qualification criteria, such as whether the interpolated flow rate $f_N$ accurately approximates the normal motion of the lungs or conversely, that the lungs maintained their normal motion during the occlusion event. Optionally, for verification, the integral of the recorded flow and the approximated normal flow between $t_0$ and $t_N$ may be required not to substantially differ. It should be noted that such an approximation is feasible as the airway occlusion event is relativity short, for example less than 150 ms, and the inertial motion of the lungs may not be significantly affected. Furthermore, it should be noted that the process may include other event qualification criteria that may be introduced at any of its stages.

In cases where the flow rate at $t_N$ is sufficiently close to the flow rate at $t_0$, $f_N$ may be approximated according to $f_0$, for example as described above. Alternatively, the verification calculation may be performed as follows:

$$\int_{t_0}^{t_1} f_N dt \sim \int_{t_1}^{t_N} (f - f_N) dt = \Delta V_{Event} - \Delta V_N$$

If the verification calculation fails, the density related pulmonary volume change calculation is discarded or restarted, as shown at 4507. Other verification indicators may be used for determining the usability of the occlusion event for calculations of density related volume changes such as the ability to accurately determine $t_2$ and $t_N$.

If the verification calculation succeeds, as shown at 4504, an instant distinguishing a change in the airflow rate ($f$,) trend, denoted herein as $t_2$ (also marked as 824 in FIG. 20) is identified between $t_{1,N}$ and $t_N$. The change in airflow rate trend may be indicative of a change in the forcing of airflow, from density-related flow release to other contributions such as normal airflow forcing and other responsive airflow forcing.

Alternatively, the instant $t_2$ may be identified as the instant during which the functional form of the airflow rate changes from an exponential time dependence to a linear time dependence. In addition or alternatively, the instant $t_2$ may be identified as the instant during which the functional form of the airflow rate changes from an exponential time dependence with a certain time constant to another exponential decay with another (e.g., different) time constant. The flow signal may optionally be transformed in order to make the distinction of the change of airflow rate trend clearer, for example, by taking the natural log of the flow signal, or by using a Fourier transform of the flow signal. Optionally, an interval in which this flow rate change is expected to occur is chosen and the instant of maximum change rate of the airflow rate may be calculated in that pre-selected interval, as for example, shown on FIG. 20, marked by 805.

Optionally, as shown at 4508, the accuracy of $t_2$ may be verified by analyzing the recorded flow rate f. For example, the flow rate f may be analyzed to determine whether it includes an abrupt change from a fast flow decrease to a mild flow decrease.

In addition, as shown at 4505, the area of the flow rate curve above the $f_N$ curve that represents a surplus volume, denoted as $\Delta V_{Surplus}$, may be calculated. This area may be calculated in a period during which the airway flow rate exceeds the normal motion of the lungs. As used herein, a normal motion of the lungs means the respiration flow rate of the user when her airways are not occluded in response to an airway occlusion event. Optionally, in order to identify this period, an instant after the reopening initiation $t_1$ during which the interpolated estimated flow rate $f_N$ and the recorded airway flow rate f are equal is identified. From the curves f and $f_N$ points of view, this instant, denoted herein as $t_{1,N}$, as shown at 5005 in FIG. 24, is the first instant after $t_1$ in which f crosses $f_N$. For example, numeral 5002 depicts an exemplary instant after $t_1$ in which f also crosses $f_N$.

The surplus pulmonary volume $\Delta V_{Surplus}$ is optionally identified by a calculation of the differences between the interpolated flow rate and the flow rate between $f(t_{1,N})$ and $f(t_2)$. This surplus volume may be calculated as follows:

$$\Delta V_{Surplus} = \Delta V + \Delta V_R = \Delta V_{Event} - \Delta V_N = \int_{t_1}^{t_N}(f - f_N) dt$$

where $\Delta V_R$, is determined under the assumption that density changes terminate more abruptly than processes involving motion of pulmonary tissues. Thus, a surplus to the flow rate that generates a relatively high flow rate curve f that terminates abruptly may be considered as an outcome of density changes.

Turning briefly to FIG. 24, the area under $f_N$ corresponds to $\Delta V_N$ and the area enclosed by the flow rate curve f and the interpolated flow rate $f_N$ corresponds to $\Delta V_{Surplus}$. As shown by $f_0$, the $f_0$ baseline is significantly different from $f_N$, emphasizing the importance of the interpolated flow. As outlined above, the surplus volume may be separated into $\Delta V$ and $\Delta V_R$ by $f_S$. $\Delta V_N$ is identified as the area under f and $f_N$ between $t_1$ and $t_N$.

Returning to FIG. 23, the flow rate contribution of the lungs' responsiveness ($\Delta V_R$) to the airway occlusion event is reduced from the surplus volume $\Delta V_{Surplus}$ for segmenting and optionally outputting $\Delta V$ at 4506. In some aspects, this may be understood herein as the expulsion or insertion of air which are affected by changes in air density in the lungs and indicative of the density of air in the lungs. Optionally $\Delta V$ may be calculated as follows:

$$\Delta V = \int_{t_{1,N}}^{t_2}(f - f_S) dt.$$

In events where $f(t_2) > f(t_{1,N})$, it may be assumed that a determination of $\Delta V$ is enabled by defining $f_S$ as follows:

$$f_S = f(t_2) - (f(t_2) - f(t_{1,N})) e^{\lambda(t - t_{1,N})^2}$$

where $\lambda$ is defined such that $f_S(t_2) = 0.99 f(t_2)$, for example as follows:

$$\lambda = \frac{\ln(0.01 f(t_2))}{\left(f(t_2) - f(t_{1,N})\right)(t_2 - t_{1,N})^2}.$$

Similarly, in cases where $f(t_2) \leq f(t_{1,N})$ it is assumed that an accurate determination of $\Delta V$ is obtained for a linear $f_S$. The best fit for $f_S$ may depend on the properties of the shutter that is used for occluding the airways and/or the chamber of the breathing device 100 and therefore other optional optimal functional forms of $f_S$ may be used. Optionally, the shutter described above, in relation to numeral 104, may be used for generating a relatively short reopening completion time that generates a relatively limited compression wave. In such an embodiment the accuracy in the determination of $t_1$, $t_2$ and the approximated $f_N$ is relatively high.

It should be noted that as the methods 4000 and 4500 described in FIGS. 21 and 23, respectively, may be based on data recorded at some stages in (and optionally after a respiratory modulation that is performed during a normal respiration of the user), a minimal patient cooperation is required. In such a manner, the density related pulmonary volume change and the alveolar pressure of small children, disabled patients, comatose patients, and/or any other low or non-cooperative patients may be determined.

Figure 25:
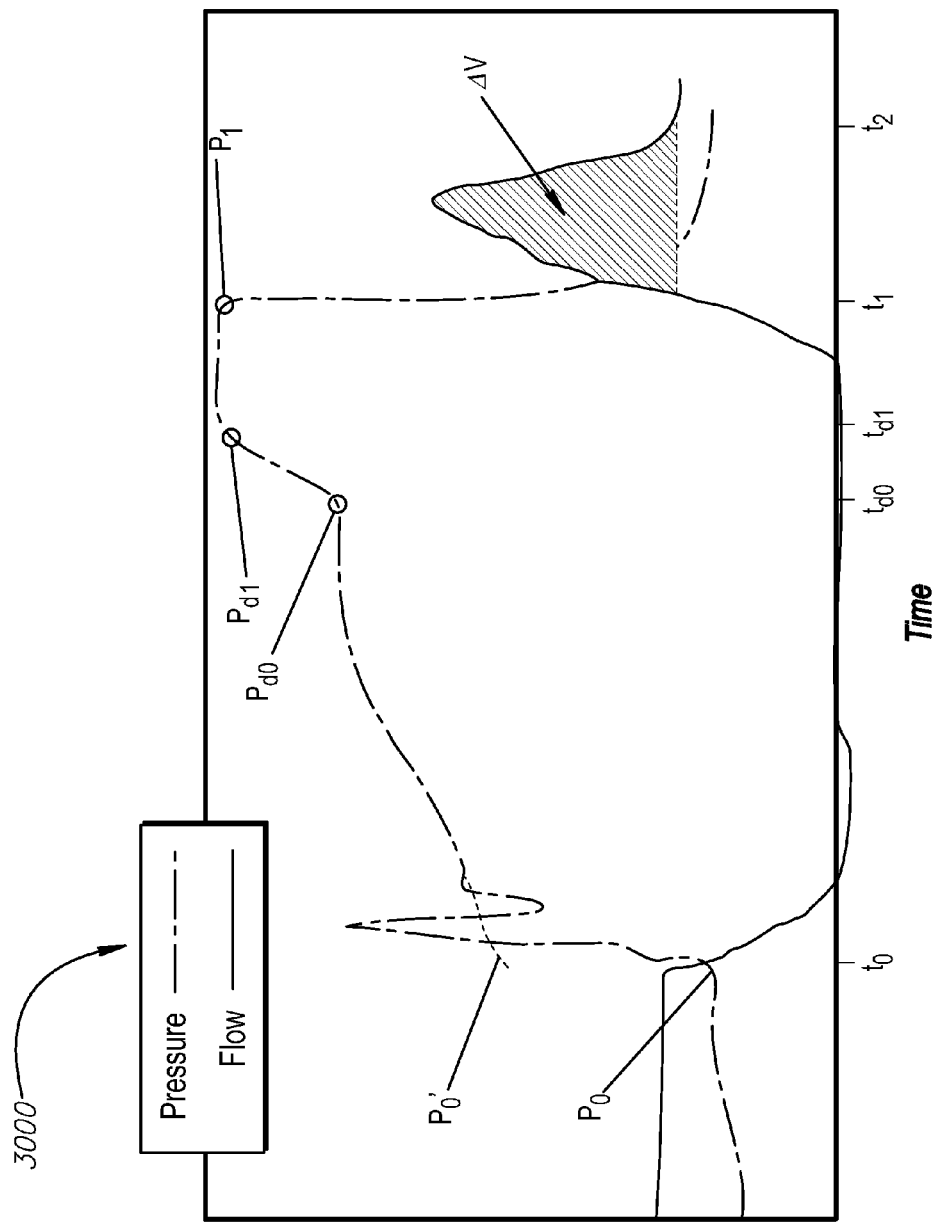
FIG. 25 is a graph depicting the time dependence of air pressure and air flow rate at the airway from a time shortly before an occlusion until shortly after an occlusion.

FIG. 25 is a graph 3000 depicting the time dependence of air pressure and air flow rate at the airway from a time shortly before an occlusion until shortly after an occlusion. Various time instants are illustrated, including a time instant $t_0$ when the occlusion event is initiated (e.g., shutter 104 closes), a time instant $t_1$ when the occlusion even terminates (e.g., shutter 104 opens); a time instant $t_2$ between a relatively steep decline in the recorded flow rate and a milder decline in the recorded flow. Additional illustrated time instants include $t_{d0}$ when an artificial change-in-volume event is initiated; and $t_{d1}$ when the artificial change-in-volume event is terminated. Further, a recorded pressure, P, is shown as a dotted line and a recorded flow, f, is shown as a solid line.

During the occlusion event the pressure change is interfered by a controlled volume change of a volume changing device (e.g., a pump, a piston, or other device). The pressure slope during interruption occlusions of interrupter devices may be dependent or entirely dependent on the maneuver performed by the patient. However, in patients who suffer from prolonged mouth and alveolar pressure equilibration or users who are unable to produce interruption events in which the deviation of the pressure from base pressure is significant, the pressure signal is either too weak or inappropriate for accurately calculating pulmonary properties such as airway resistance and lung volume. This can be remedied by enhancing the pressure signal after full mouth and alveolar pressure equilibration has been achieved.

For example, FIG. 25, may depict an occlusion event in which the deviation of alveolar pressure from base pressure is enhanced by a controlled mechanical change of volume, (i.e., not through the normal motion of the lungs). The contraction or expansion of volume is performed by a pump, such as pump 302, connected to flow tube 304, as described in FIG. 22. For clarity, pump 302 may propel air away from the chamber, thereby to induce expiration or resist inspiration. Optionally, the pump 302 may propel air into the chamber, and thereby induce inspiration or resist expiration. In some aspects, the pump 302 is located between the mouth of the user and the shutter 104. Optionally, the pump 302 injects or extracts air from the portion at a rate that is significantly faster than the airflow rate of respiration at the instant of measurement. Optionally, the shutter 104 is located between the mouth of the user and the pump 302. Further, in some aspects, the chamber 101 is connected to an external container of varying volumetric capacity.

As illustrated, the closable flow tube 304 is a T shaped tube that allows the airflow in the breathing device to bypass the shutter 104. Optionally, the closable flow tube 304 is a T shaped tube that directs airflow into a sealed container. In some embodiments, the flow tube 304 is an isothermal container, such that it can be regarded as a continuation of the lungs. The closable flow tube 304 may be closed, automatically and/or manually, at one or more velocities.

If, during the mechanical change in volume, the system remains closed (in the sense that the total number of molecules of the system, comprising the lungs and mechanical apparatus, is constant), and if the controlled mechanical change in volume is small in comparison to the instantaneous volume of the lungs, then the change in pressure occurring due to the change in volume will obey Boyle's law. Thus, as depicted in FIG. 25, the amplitude of both $\Delta P$ and $\Delta V$ of Boyle's law, as written above, may be artificially increased, independent of the normal breathing of the user. Such an increase in $\Delta P$ and $\Delta V$ may improve the signal to noise ratio, thus improving the accuracy of the measurement. In addition, increasing the proportion of $\Delta V$ with respect to $\Delta V_{Surplus}$ may allow for a clearer identification of $t_2$, as described above and shown on FIG. 24. In addition, the increased signal to noise ratio allowed by the artificial change in volume may reduce the level of cooperation required from the user. Optionally, the user may be completely static and the change in alveolar pressure during the occlusion is produced entirely by the pump.

In some embodiments, indicators of lung compliance are calculated and/or correlated according to the instantaneous lung volume and/or the alveolar pressure $P_{Al}$. Lung Compliance, denoted herein as $C_L$, may be defined as follows:

$$C_L = \frac{V_a - V_b}{P_a - P_b}$$

where V and P denote the lung volume and pressure, respectively, under static conditions, and the indices a and b refer to two different static lung states (with $V_a > V_b$). Lung compliance is a measure of the elasticity of the lung tissue. For example, patients suffering from emphysema are generally observed to have an above normal lung compliance while patients suffering from fibrotic lung conditions are observed to have a below normal lung compliance.

In the example shown in FIG. 25, an artificial change in volume, beginning at the instant denoted as $t_{d0}$ and ending at the instant denoted as $t_{d1}$, produces the change in pressure $P_{d1} - P_{d0}$. Letting dV denote the artificially controlled change in volume and due to the elasticity of the lungs, a part of dV, denoted here as $\delta V$, may produce reinflation/deflation of the lungs. The remaining part of dV, as above denoted by $\Delta V$, may affect the density of the air in the lungs, so that $dV = \delta V + \Delta V$. Lung compliance at the instant of occlusion, denoted as $C_0$, may then be calculated as $$C_0 = \frac{\delta V}{P_{d1} - P_{d0}}.$$

If the controlled change in volume and the instantaneous volume of the lungs are known, from Boyle's law, $C_0$ is given by $$C_0 = \frac{dV}{P_{d1} - P_{d0}} - \frac{V_0}{P_A}$$

where as above, $V_0$ denotes the instantaneous volume of the lungs and $P_A$ denotes the ambient pressure at the instant of the occlusion.

Figure 26:
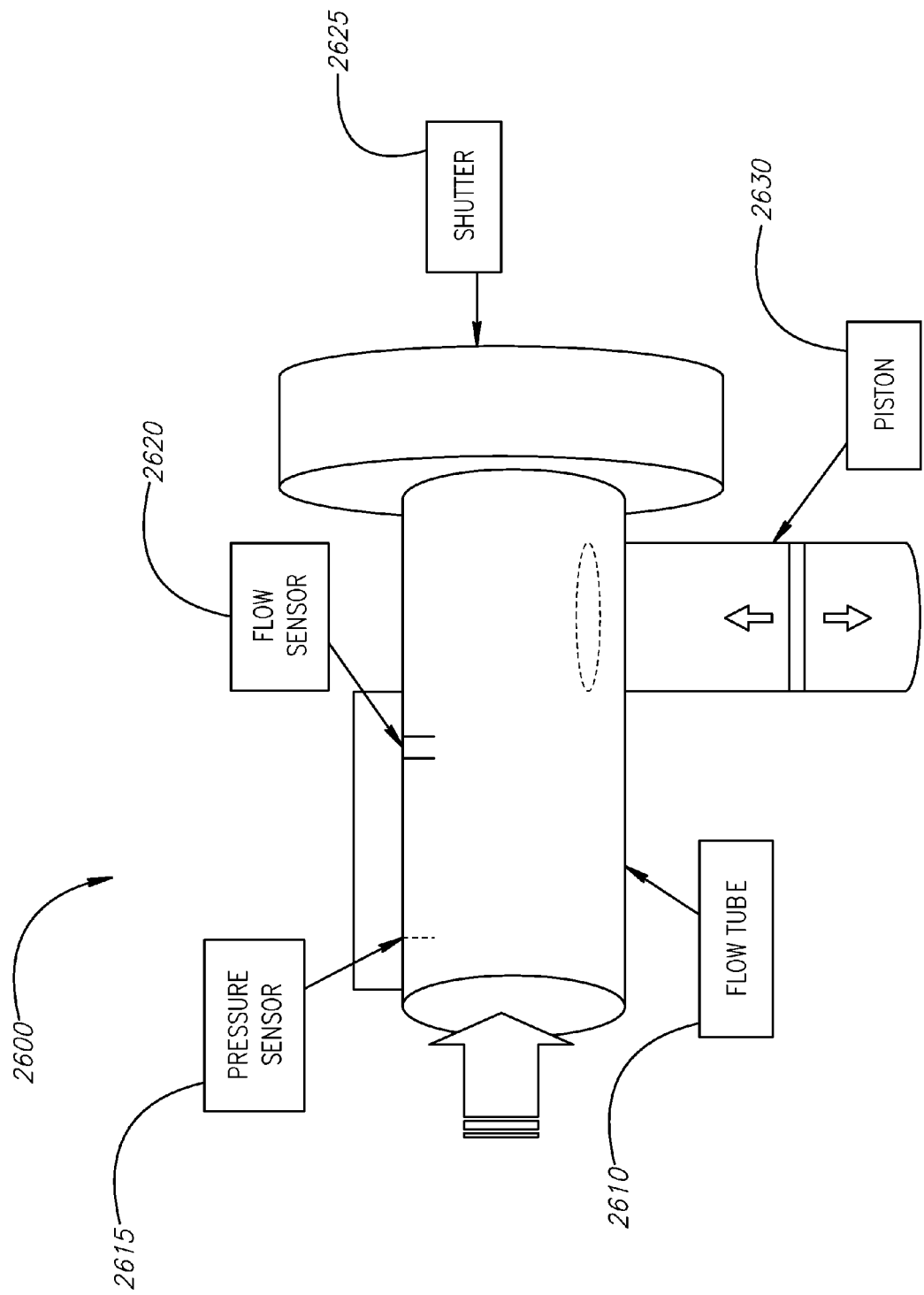
FIG. 26 illustrates an exemplary breathing device for artificially controlling a volume change.

For example, turning to FIG. 26, an exemplary breathing device 2600 for artificially controlling a volume change is illustrated. The illustrated device 2600 includes a flow tube 2610, a pressure sensor 2615, a flow sensor 2620, a shutter 2625, and a piston 2630. In some embodiments of the device 2600, the sensors 2615 and 2620 may be substantially similar to the sensors 105 and 109, respectively, illustrated in FIG. 17. Alternatively, the pressure sensor 2615 may be any device that can measure a pressure of airflow in the flow tube 2610. Further, the flow sensor 2620 may be any device that measures a flow rate of the airflow in the flow tube 2610. Shutter 2625 may be substantially similar to the shutter 104 illustrated in the FIG. 17 and may initiate an occlusion event as described above.

The piston 2630 may operate to provide an artificial change in volume as described above, in place of, for example a pump such as pump 302. More specifically, the piston 2630 may operate to: propel air away from the tube 2610, thereby to induce expiration or resist inspiration; or propel air into the tube 2610, and thereby induce inspiration or resist expiration. Thus, the piston 2630 may operate to create a mechanical change in volume during an occlusion event (i.e., while the system remains closed). As described above, if the controlled mechanical change in volume is small in comparison to the instantaneous volume of the lungs, then the change in pressure occurring due to the change in volume will obey Boyle's law. Thus, the amplitude of both $\Delta P$ and $\Delta V$ of Boyle's law may be artificially increased independent of the normal breathing of the user so as to improve the signal to noise ratio and the accuracy of the measurement.

Returning to FIG. 20, which illustrates one embodiment of the GUI 800 depicting parameters and graphs of variables relevant for lung volume measurement, a panel 821 showing a plot of the volume change over time 814 of the entire measurement may also be depicted on the GUI 800. The panel 821 may also show the timing of the occlusion event in respect to the total duration of the measurement 817, a TLC reference volume line 815, and a TGV or RV reference line 816.

GUI 800 may also include a panel showing a plot of the flow line 801 and pressure after the shutter opening. This panel may also display an interval 805 in which $t_2$ exists and the exact instant of $t_2$ 824. Optionally this panel also shows the $f_S$ line 802, as described above. This panel may also show an $f_0$ baseline 804 and an $f_N$ line 803, as described above.

In some aspects, the GUI 800 includes a panel 808 showing the interval shortly before and after the shutter closing. This panel may display the instant of occlusion 823. Further, this panel may display the calculated alveolar pressure at the instant of occlusion 818. Optionally the color of the line denoting the value of the alveolar pressure at the instant of occlusion, denoted as $P_0'$, is indicative of the potential calculation error of this pressure value. For example, a green line color may indicate that the approximated error of the calculation of $P_0'$ is relatively small while a red color may indicate that the error is significant and the calculation of instantaneous volume of the current occlusion event should be ignored. Optionally, this panel may also show the pressure line and the extrapolated pressure line.

In some aspects, the GUI 800 also includes a panel showing a plot of the flow and pressure lines shortly before and after the occlusion event. This panel may also show the instant 813 from which back extrapolation of the pressure curve begins. Further, this panel may also show $P_1$, the pressure level at the instant of shutter opening.

The GUI 800 may also include a panel 812 showing a plot of the flow and pressure lines during the respiratory half cycle corresponding to the occlusion event being analyzed. Optionally the timing of the occlusion event in the respiratory half cycle may be displayed.

In some aspects, the GUI 800 may include a panel 822 of tools for calculating and manually setting the value of $t_2$, $t_1$, $P_0'$, and $P_1$. Optionally the GUI 800 includes tools for browsing and sorting occlusion events. Further, in some aspects, the GUI 800 may display a quality rating, QR 806, denoting the quality of the occlusion event. Optionally the GUI 800 may display the number of valid events, qualifying pre-selection criteria. Optionally the GUI 800 may display $\Delta V$, the duration of the event, the pressure level of $P_1$, $P_0'$ and $\Delta P$. In some aspects, the GUI 800 may display the statistical validity 820 of the measurement.

A number of embodiments have been described, and several others have been mentioned or suggested. Other embodiments are within the scope of the disclosure and claims. For instance, in some embodiments described above, the signal processing that is described is carried out based upon pressure and flow signals generated by a flow interruption (e.g., an occlusion event). Moreover, those signals are measured close to a mouth of a subject and subsequent calculations are computed in the time domain. In some instances, however, flow interruption methods described above and forced oscillation methods to measure respiratory system input impedance may be substantially similar and/or equivalent. Further, the flow interruption methods and forced oscillation methods may be related (e.g., directly) mathematically by a Fourier transformation. See Peslin, R., Fredberg, J. J., "Oscillation Mechanics of the Respiratory System," P. Macklem, J. Mead, Editors. Handbook of Physiology: The Respiratory System III, Mechanics of Breathing. American Physiological Society. 145-177, 1986. For any given signal bandwidth, the information contained in one measurement is identical to the information contained in the other—in other words, flow interruption and respiratory impedance measurements may be functionally equivalent. Thus, if absolute lung volume can be ascertained as revealed above, so too can they be ascertained by the forced oscillation technique and respiratory impedance measurement. Prior efforts and/or techniques, however, may not include a method to obtain absolute lung volumes from forced oscillation measurements and respiratory impedance data. See FARRE, R., R. PESLIN, E. OOSTVEEN, B. SUKI, C. DUVIVIER, AND D. NAVAJAS. Human respiratory impedance from 8 to 256 Hz corrected for upper airway shunt. J. Appl. Physiol. 67(5): 1973-1981, 1989. As such, the techniques described herein may allow for the determination of absolute lung volumes from forced oscillation measurements and respiratory impedance data. Furthermore, those skilled in the art will readily recognize additional advantages that a variety of additions, deletions, alterations, and substitutions may be made to these embodiments.

What is claimed is:

1. A method for determining a pulmonary volume change, comprising:
receiving a respiration cycle from a subject in an airflow chamber;

interrupting the respiration cycle by an occlusion of the airflow chamber initiated at a first time instant and terminated at a second time instant subsequent to the first time instant;

taking a plurality of measurements of airflow rate through the airflow chamber between the second time instant and a third time instant subsequent to the second time instant; and determining a pulmonary volume change substantially equal to a reduction of a pulmonary air volume by a pulmonary response air volume and a normal air volume, wherein the pulmonary volume change is related to a change in density of air in the airflow chamber.

2. The method of claim 1, wherein determining a pulmonary volume change substantially equal to a reduction of a pulmonary air volume by a pulmonary response air volume and a normal air volume comprises:

determining a pulmonary air volume based on the plurality of measured airflow rates;

determining a normal air volume; and determining a pulmonary response air volume between a fourth time instant and a fifth time instant.

3. The method of claim 2, wherein determining a normal air volume comprises:

determining a normal airflow rate during the respiration cycle between the second time instant and the third time instant, wherein the normal airflow rate is substantially equal to an airflow rate that would have existed between second and third time instants in the absence of the interruption by the occlusion of the airflow chamber; and integrating the normal airflow rate between the second and third time instants.

4. The method of claim 3, wherein determining a normal airflow rate during the respiration cycle between the second time instant and the third time instant comprises:

measuring a normal airflow rate for a time period prior to the first time instant;

measuring the normal airflow rate for a time period subsequent to the third time instant; and determining the normal airflow rate between the second and third time instants by interpolating from the measured normal airflow rates prior to the first time instant and subsequent to the third time instant.

5. The method of claim 4, wherein the interpolation comprises one of:

a spline interpolation;

an exponential interpolation; and a polynomial interpolation.

6. The method of claim 3, wherein determining a normal airflow rate during the respiration cycle between the second time instant and the third time instant comprises:

measuring at least one of a normal airflow rate for a time period prior to the first time instant and the normal airflow rate for a time period subsequent to the third time instant; and determining the normal airflow rate between the second and third time instants by extrapolation from one of the measured normal airflow rate prior to the first time instant and the measured normal airflow rate subsequent to the third time instant.

7. The method of claim 3, wherein determining a normal airflow rate during the respiration cycle between the second time instant and the third time instant comprises:

measuring at least one of a normal airflow rate for a time period prior to the first time instant, measuring pressure between the first time instant and the second time instant; and determining the normal airflow rate between the first time instant and the second and third time instants by relating changes in pressure with changes in normal airflow rate.

8. The method of claim 3, wherein determining a pulmonary response air volume between a fourth time instant and a fifth time instant comprises:

determining a fourth time instant when the measured airflow rate is initially substantially equal to the normal airflow rate subsequent to the second time instant;

determining a fifth time instant when a trend change in the measured airflow rate occurs, subsequent to the second and fourth time instants;

determining a pulmonary response airflow rate between the fourth and fifth time instants; and integrating the pulmonary response airflow rate between the fourth and fifth time instants inclusively.

9. The method of claim 8, further comprising:

integrating the pulmonary response airflow rate between the fifth and third time instants inclusively; and reducing the integral of the normal flow rate between the second and third time instants.

10. The method of claim 1, wherein interrupting the respiration cycle by an occlusion of the airflow chamber comprises applying an external pressure on a combination of a portion of the subject's pulmonary system and the airflow chamber.

11. The method of claim 1, wherein taking a plurality measurements of airflow rate through the airflow chamber comprises:

measuring a pressure change in the airflow chamber during the respiration cycle at a plurality of instants between the second time instant and the third time instant.

12. The method of claim 11, further comprising converting the measured pressure changes to a plurality of airflow rates related to the measured pressure changes and one or more dimensions of the airflow chamber.

13. The method of claim 1, further comprising:

determining an instantaneous volume of air in the lungs of the subject based on the pulmonary volume change.

14. The method of claim 13, wherein determining an instantaneous volume of air in the lungs of the subject based on the pulmonary volume change comprises:

determining a change in pressure in the lungs of the subject;

determining a base pressure substantially equal to atmospheric pressure; and calculating the instantaneous volume of air in the lungs of the subject based on the pulmonary volume change, the change in pressure in the lungs, and the base pressure.

15. The method of claim 14, wherein the instantaneous volume of air in the lungs of the subject is substantially equal to an instantaneous volume of air in the lungs of the subject at the first time instant.

16. The method of claim 14, wherein determining a change in pressure in the lungs of the subject comprises:

measuring a pressure in the airflow chamber at the first time instant;

measuring a pressure in the airflow chamber at the second time instant;

calculating a difference between the measured pressures at the first and second time instants, wherein the change in pressure in the lungs of the subject is substantially equal to the calculated difference.

17. The method of claim 13, further comprising:

determining a residual volume of air in the lungs of the subject based on the determined instantaneous volume of air in the lungs of the subject.

18. The method of claim 17, wherein determining a residual volume of air in the lungs of the subject based on the determined instantaneous volume of air in the lungs of the subject comprises:
   determining a difference between the determined instantaneous volume of air in the lungs of the subject and a maximum volume of air expirable by the subject during the respiration cycle, wherein the residual volume of air in the lungs of the subject is substantially equal to the determined difference.

19. The method of claim 17, further comprising:
   determining a total lung capacity of the subject based on the determined residual volume of air in the lungs of the subject.

20. The method of claim 17, wherein determining a total lung capacity of the subject based on the determined residual volume of air in the lungs of the subject comprises:
   determining a sum of the determined residual volume and a vital capacity of the subject, the vital capacity substantially equal to a maximum amount of air inhalable or exhalable from the subject, the total lung capacity substantially equal to the determined sum.

21. The method of claim 17, further comprising:
   determining a thoracic gas volume of the subject based on the determined residual volume of air in the lungs of the subject.

22. The method of claim 21, wherein determining a thoracic gas volume of the subject based on the determined residual volume of air in the lungs of the subject comprises:
   determining a sum of the determined residual volume and an expiratory reserve volume, the expiratory reserve volume substantially equal to a volume of air exhalable from the subject after a normal exhalation of air from the lungs of the subject, the thoracic gas volume substantially equal to the determined sum.

23. The method of claim 22, wherein the expiratory reserve volume is determined through a spirometrical measurement.

24. The method of claim 1, wherein at least a portion of the airflow chamber is kept at isothermal conditions.

* * * * *